United States Patent
Guggenheimer et al.

(10) Patent No.: US 10,905,459 B2
(45) Date of Patent: Feb. 2, 2021

(54) TISSUE-REMOVING CATHETER, TISSUE-REMOVING ELEMENT, AND METHOD OF MAKING SAME

(71) Applicant: Covidien LP, Mansfield, MA (US)

(72) Inventors: Ethan Andrew Guggenheimer, Minnetonka, MN (US); Victoria Schuman, Minneapolis, MN (US); Lucas Schneider, Champlin, MN (US); Benjamin Robert Fruland, Blaine, MN (US)

( * ) Notice: Subject to any disclaimer, the term of this patent is extended or adjusted under 35 U.S.C. 154(b) by 974 days.

(21) Appl. No.: 15/175,784

(22) Filed: Jun. 7, 2016

(65) Prior Publication Data

US 2016/0354110 A1 Dec. 8, 2016

Related U.S. Application Data

(60) Provisional application No. 62/172,597, filed on Jun. 8, 2015.

(51) Int. Cl.
*A61B 17/3207* (2006.01)

(52) U.S. Cl.
CPC ........... *A61B 17/320758* (2013.01); *A61B 2017/320791* (2013.01)

(58) Field of Classification Search
CPC ....... A61B 2017/320024; A61B 2017/320791; A61B 2017/320775; A61B 5/15126; A61B 5/15132; A61B 2017/00526; A61B 17/1615; Y10T 408/8957; Y10T 408/899; Y10T 408/90; Y10T 408/901; Y10T 408/904; Y10T 408/9042; Y10T 408/9044; Y10T 408/9045; Y10T 408/9046; Y10T 408/90467; Y10T 408/90473;
(Continued)

(56) References Cited

U.S. PATENT DOCUMENTS

| | | | |
|---|---|---|---|
| 4,729,763 A * | 3/1988 | Henrie | A61B 17/320758 604/22 |
| 4,925,216 A | 5/1990 | Steer | |
| 5,084,010 A | 1/1992 | Plaia et al. | |

(Continued)

FOREIGN PATENT DOCUMENTS

| | | |
|---|---|---|
| EP | 1 058 516 B1 | 11/2005 |
| EP | 1 158 910 B1 | 10/2007 |

(Continued)

*Primary Examiner* — Jocelin C Tanner
(74) *Attorney, Agent, or Firm* — Stinson LLP

(57) ABSTRACT

A tissue-removing catheter includes a tissue-removing element operably connected to a drive shaft for rotation of the tissue-removing element about an axis of rotation in a cutting direction. The tissue-removing element is an integrally formed, one-piece body and has an annular tissue-removing head at the distal end of a tissue-removing element body. In some embodiments, primary tissue-removing components include an integrally formed cutting tooth and inner shearing member and are spaced angularly around the tissue-removing blade. Secondary tissue-removing components include cutting teeth and are interposed between the primary tissue-removing components around the tissue-removing blade. The tissue-removing element is made by removing material from a blank to form the primary and secondary tissue-removing components.

18 Claims, 25 Drawing Sheets

(58) Field of Classification Search
CPC ............. Y10T 408/905; Y10T 408/906; Y10T 408/909; Y10T 408/9093; Y10T 408/9095
See application file for complete search history.

(56) References Cited

U.S. PATENT DOCUMENTS

| | | | |
|---|---|---|---|
| 5,351,595 | A | 10/1994 | Johnston |
| 5,507,760 | A * | 4/1996 | Wynne ............ A61B 17/320783 606/159 |
| 5,651,781 | A | 7/1997 | Grace |
| 5,919,203 | A | 7/1999 | Husted et al. |
| 6,136,014 | A | 10/2000 | Sirimanne et al. |
| 6,451,036 | B1 | 9/2002 | Heitzmann et al. |
| 6,461,357 | B1 * | 10/2002 | Sharkey ................ A61B 18/148 606/45 |
| 6,623,496 | B2 | 9/2003 | Snow et al. |
| 6,666,874 | B2 | 12/2003 | Heitzmann et al. |
| 6,685,707 | B2 | 2/2004 | Roman et al. |
| 6,997,934 | B2 | 2/2006 | Snow et al. |
| 7,171,798 | B1 | 2/2007 | Bernardy |
| 7,172,610 | B2 | 2/2007 | Heitzmann et al. |
| 7,666,134 | B2 | 2/2010 | Eriksson et al. |
| 7,842,058 | B2 | 11/2010 | Simpson et al. |
| 8,070,762 | B2 | 12/2011 | Escudero et al. |
| 8,215,533 | B2 | 7/2012 | Viola |
| 8,236,016 | B2 | 8/2012 | To et al. |
| 8,262,585 | B2 | 9/2012 | Thompson et al. |
| 8,308,746 | B2 | 11/2012 | Pravong et al. |
| 8,337,516 | B2 | 12/2012 | Escudero et al. |
| 8,361,094 | B2 | 1/2013 | To et al. |
| 8,469,981 | B2 | 6/2013 | Robertson et al. |
| 8,475,483 | B2 | 7/2013 | Schmitz et al. |
| 8,496,677 | B2 * | 7/2013 | Zhang ............ A61B 17/320783 606/159 |
| 8,531,064 | B2 | 9/2013 | Robertson et al. |
| 9,687,266 | B2 * | 6/2017 | Moberg ......... A61B 17/320758 |
| 2002/0049438 | A1 * | 4/2002 | Sharkey ............. A61B 18/1402 606/41 |
| 2002/0077642 | A1 | 6/2002 | Patel et al. |
| 2003/0014050 | A1 * | 1/2003 | Sharkey ............... A61B 18/148 606/45 |
| 2004/0193150 | A1 * | 9/2004 | Sharkey ............. A61B 18/1402 606/41 |
| 2007/0266833 | A1 | 11/2007 | Radziszewski et al. |
| 2008/0154296 | A1 * | 6/2008 | Taylor ..................... A61B 1/32 606/190 |
| 2010/0256527 | A1 | 10/2010 | Lippert et al. |
| 2010/0256528 | A1 | 10/2010 | Lippert et al. |
| 2010/0256601 | A1 | 10/2010 | Lippert et al. |
| 2010/0256602 | A1 | 10/2010 | Lippert et al. |
| 2010/0256606 | A1 | 10/2010 | Lippert et al. |
| 2011/0054507 | A1 | 3/2011 | Batten et al. |
| 2011/0098711 | A1 | 4/2011 | Batten et al. |
| 2012/0022564 | A1 | 1/2012 | Batten et al. |
| 2012/0046679 | A1 | 2/2012 | Patel et al. |
| 2012/0123352 | A1 * | 5/2012 | Fruland ................ A61B 5/0066 604/264 |
| 2012/0296277 | A1 | 11/2012 | Summerville et al. |
| 2013/0096587 | A1 | 4/2013 | Smith et al. |
| 2014/0128893 | A1 * | 5/2014 | Guggenheimer ........................... A61B 17/320758 606/159 |
| 2014/0171987 | A1 * | 6/2014 | Schneider .......... A61B 17/3207 606/159 |
| 2014/0222045 | A1 * | 8/2014 | Schneider ...... A61B 17/320783 606/159 |

FOREIGN PATENT DOCUMENTS

| | | |
|---|---|---|
| EP | 1 870 044 B1 | 7/2009 |
| EP | 1 957 134 B1 | 8/2011 |
| WO | 2007/067449 A2 | 6/2007 |
| WO | 2010/077692 A2 | 7/2010 |
| WO | 2010/121172 A1 | 10/2010 |
| WO | 2012/003430 A2 | 1/2012 |
| WO | 2013/049734 A1 | 4/2013 |

* cited by examiner

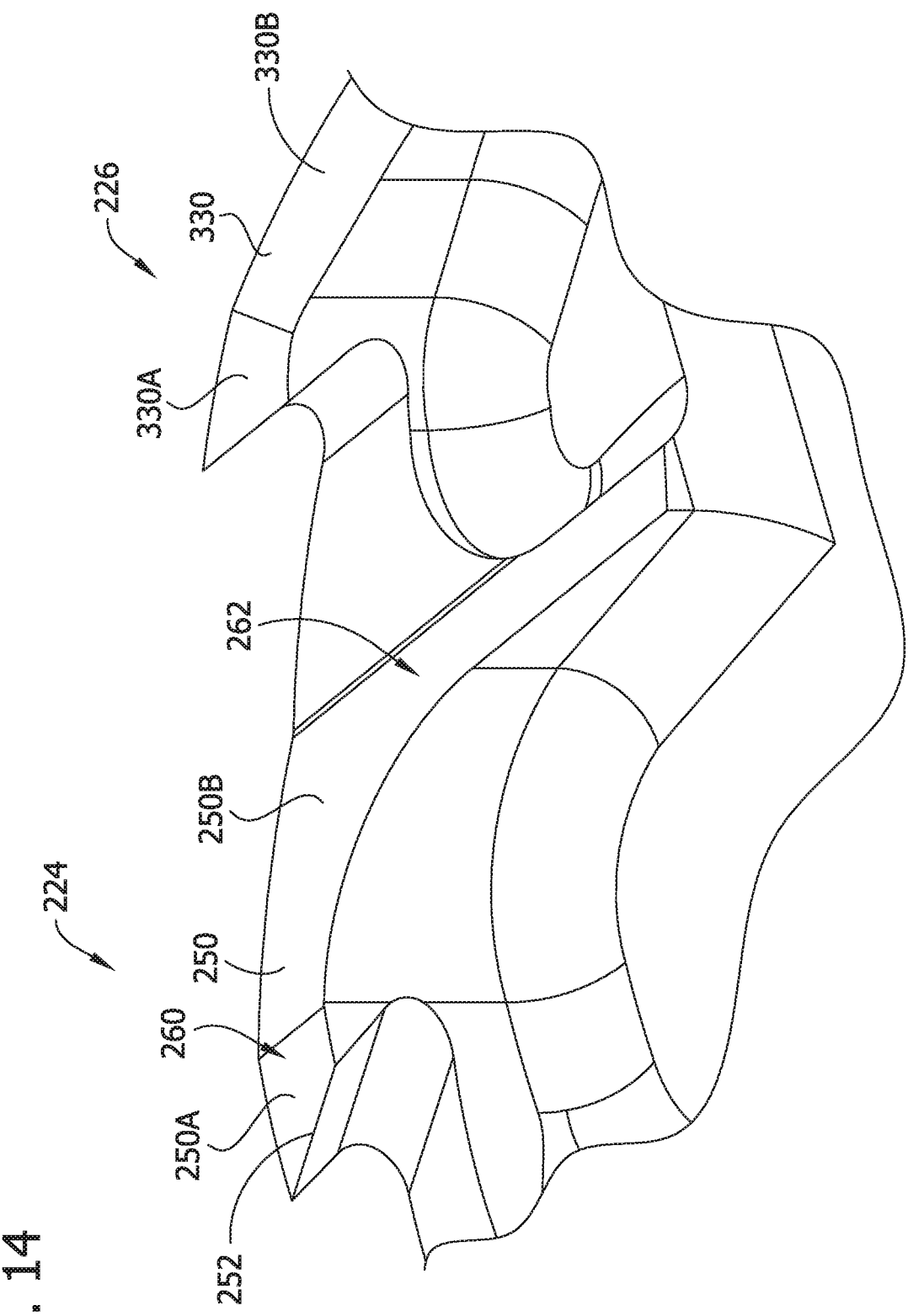

TISSUE-REMOVING CATHETER, TISSUE-REMOVING ELEMENT, AND METHOD OF MAKING SAME

CROSS-REFERENCE TO RELATED APPLICATIONS

The present application claims the benefit of U.S. Provisional Application Ser. No. 62/172,597, filed Jun. 8, 2015, the entirety of which is hereby incorporated by references herein.

FIELD OF THE DISCLOSURE

The present disclosure generally relates to a tissue-removing catheter, tissue-removing element thereof, and method of making the tissue-removing element.

BACKGROUND OF THE DISCLOSURE

Catheters are used to remove unwanted tissue from the body. As an example, atherectomy catheters are used to remove material from a blood vessel to open the blood vessel and improve blood flow through the vessel.

SUMMARY OF THE DISCLOSURE

A tissue-removing catheter includes a tissue-removing element operably connected to a drive shaft for rotation of the tissue-removing element about an axis of rotation in a cutting direction. The tissue-removing element is an integrally formed, one-piece body and has an annular tissue-removing head at the distal end of a tissue-removing element body. Primary tissue-removing components include an integrally formed cutting tooth and inner shearing member and are spaced angularly around the tissue-removing head. Secondary tissue-removing components include cutting teeth and are interposed between the primary tissue-removing components around the tissue-removing head. As the tissue-removing element rotates in the cutting direction and advances axially through a body lumen, the cutting teeth cut into and/or through tissue in the lumen. Some tissue rides along a radially inner surface of the cutting teeth as the tissue rotates and is sheared radially inwardly by the inner shearing member. In certain embodiments, the cutting teeth have a somewhat rectangular cross-sectional shape so that the cutting teeth bite through tissue. In other embodiments, the cutting teeth can have a beveled leading portion that slices through the tissue to shear it radially inwardly. The tissue-removing element is made by removing material from a blank to form the primary and secondary tissue-removing components.

Other objects and features will be in part apparent and in part pointed out hereinafter.

BRIEF DESCRIPTION OF THE DRAWINGS

FIG. 14 is a fragmentary perspective of the tissue-removing element of FIG. 13;

Corresponding reference characters indicate corresponding parts throughout the drawings.

DETAILED DESCRIPTION

Figure 1:
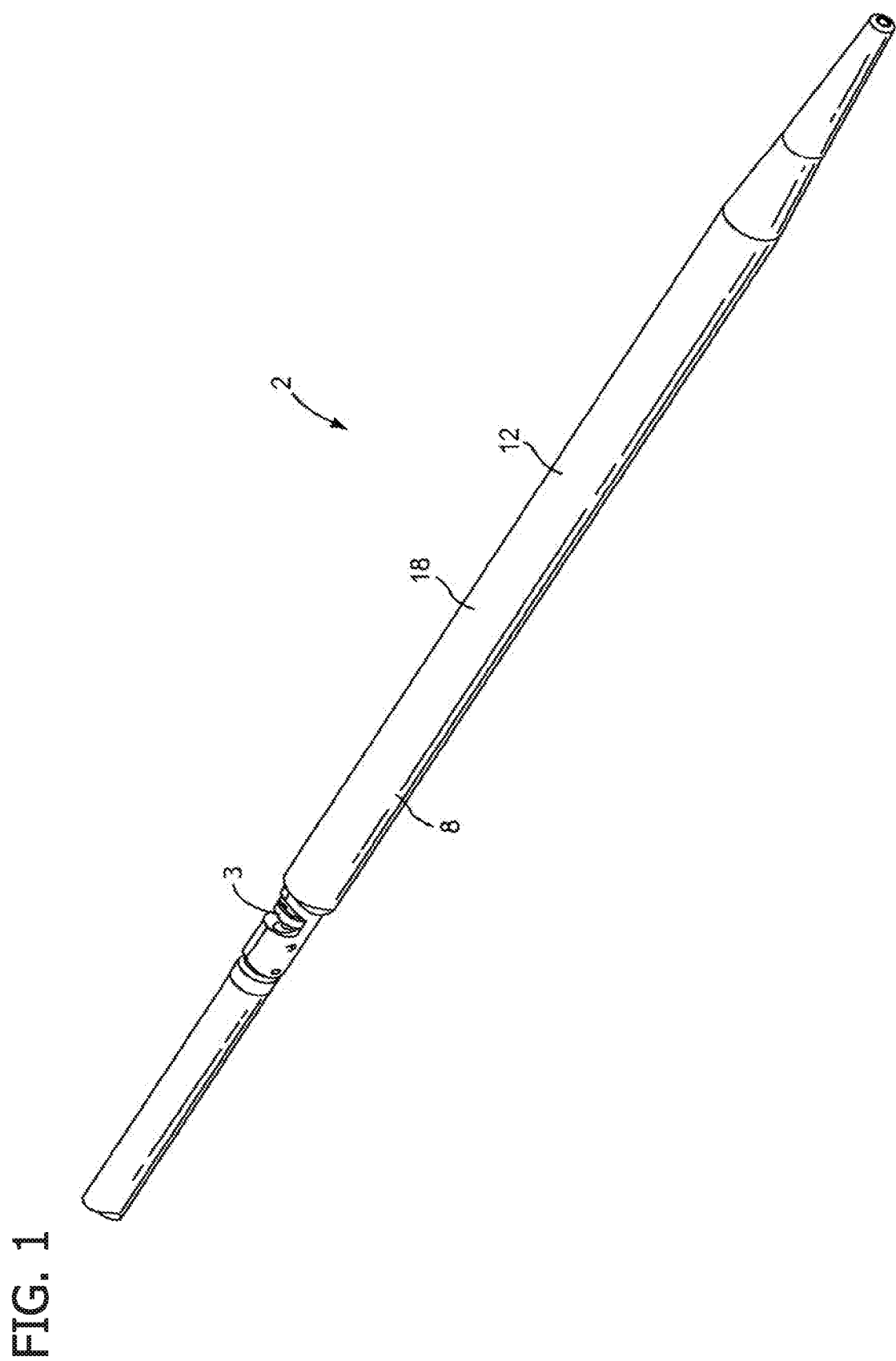
FIG. 1 is a perspective of a distal end of an atherectomy catheter.

Referring now to the drawings, several embodiments of a tissue-removing catheter for removing tissue from a body lumen are disclosed. In particular, the illustrated catheter embodiments are suitable for removing tissue from a body lumen wall, and are particularly suitable for removing (i.e., excising) plaque tissue from a vessel wall (e.g., peripheral arterial or peripheral venous wall). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from and penetrating occlusions in blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Figure 2:
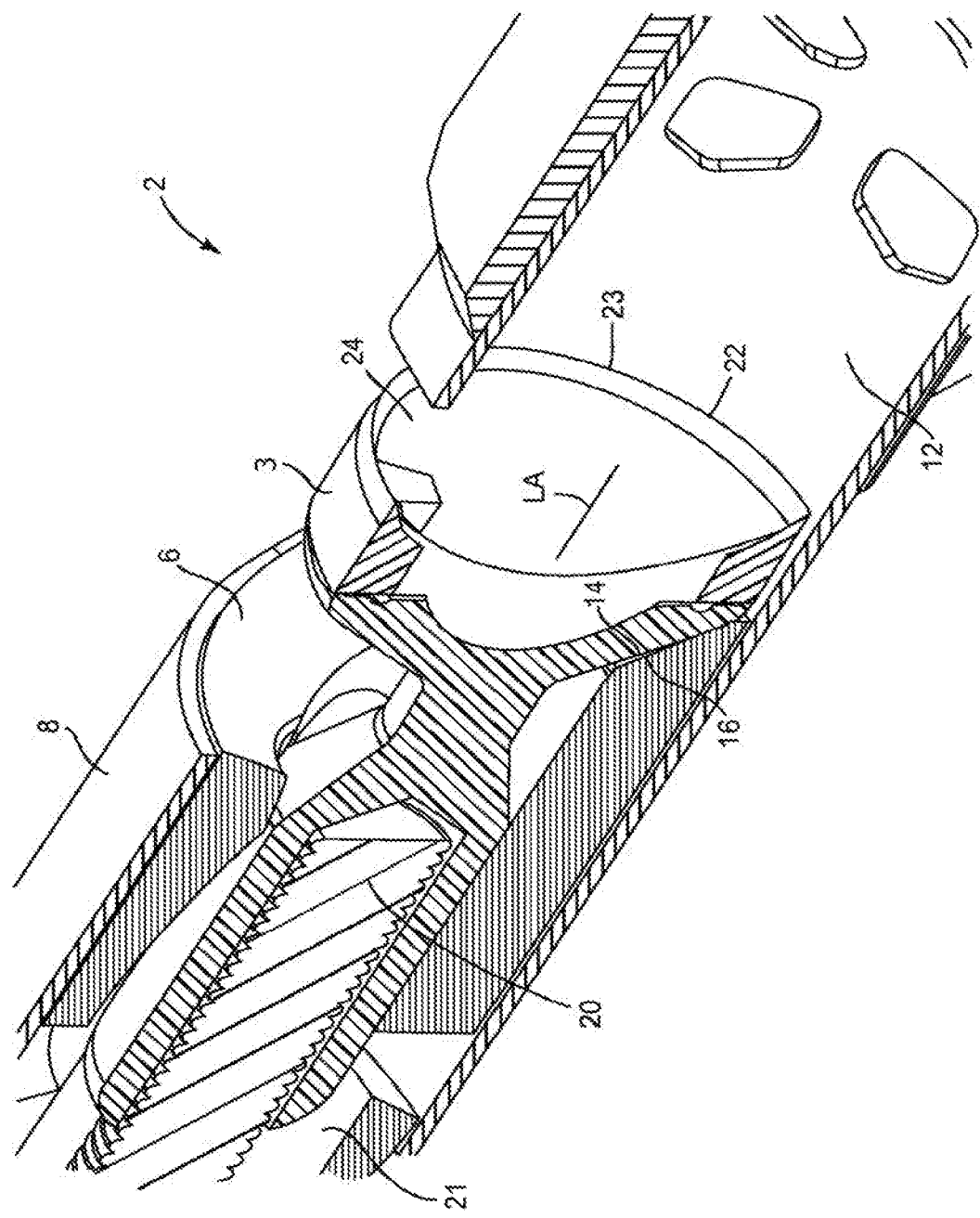
FIG. 2 is an enlarged fragmentary section of the atherectomy catheter of FIG. 1, illustrating one embodiment of a tissue-removing element in a stowed position.
Figure 3:
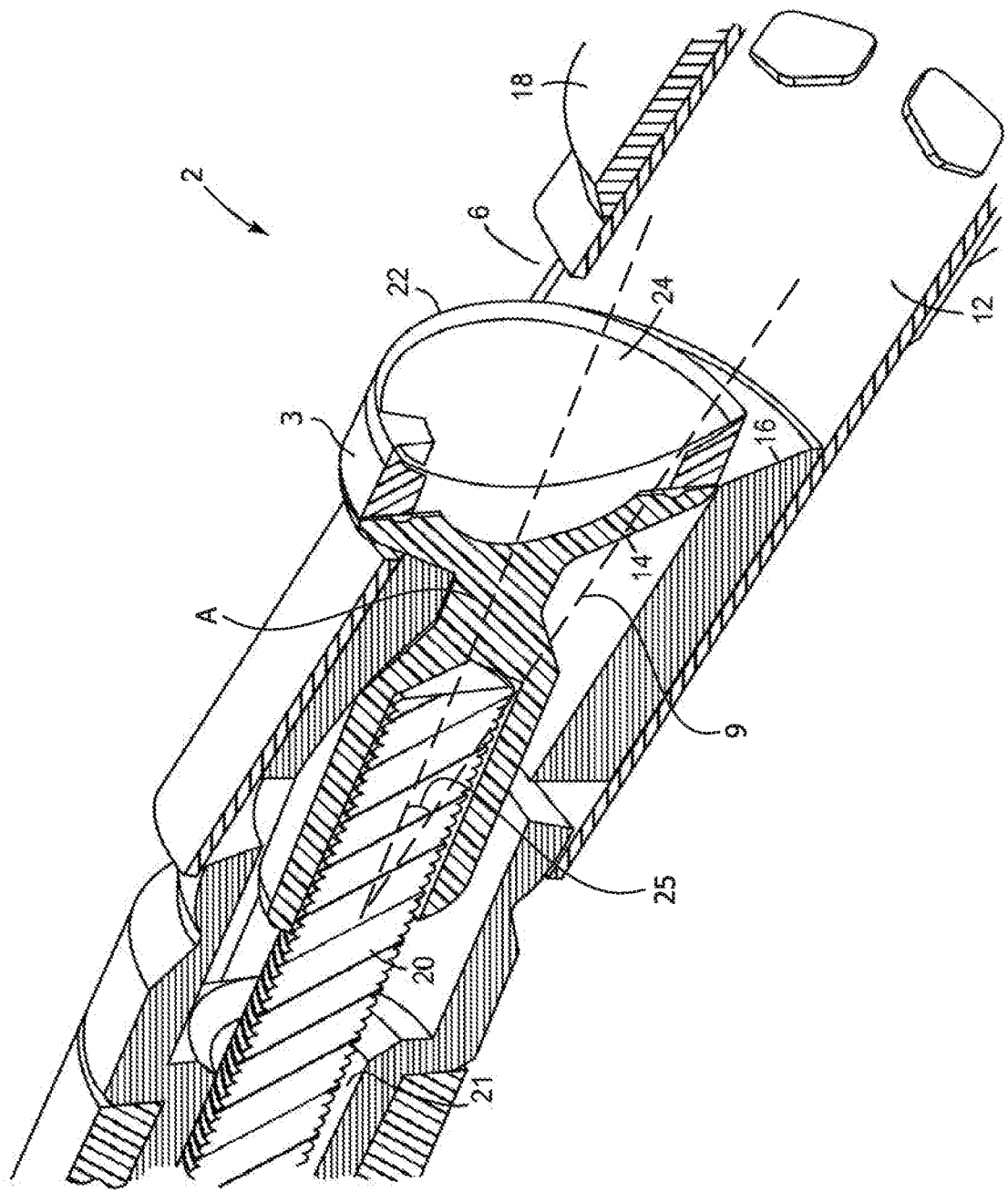
FIG. 3 is the enlarged fragmentary section of FIG. 1, illustrating the tissue-removing element in a deployed position.

Referring to FIGS. 1 to 3, an atherectomy catheter 2 (broadly, a "tissue-removing catheter"), which has a tissue-removing element 3 (broadly, a "tissue-removing element"), is used to cut material from a body lumen. The tissue-removing element 3 illustrated in FIGS. 1 to 3 is a conventional tissue-removing element. As will be explained below, tissue-removing element embodiments described in the present application are suitable replacements for the conventional tissue-removing element 3. That is, the tissue-removing element embodiments described herein below are suitable for use with the illustrated catheter 2 in place of the conventional tissue-removing element 3. The catheter 2 has an elongate body 8 having distal and proximal portions and sized and shaped for insertion into a body lumen of a subject. The tissue-removing element 3 is movable between a stored position (FIG. 2) and a cutting position (FIG. 3) relative to a window or opening 6 in the catheter body 8 adjacent the distal portion. The tissue-removing element 3 moves outwardly relative to the opening 6 so that an exposed portion of the element 3 extends outside the body 8 through the opening 6. The tissue-removing element 3 may be positioned relative to the body 8 and opening 6 so that less than 90 degrees of the tissue-removing element 3 is exposed to cut tissue. Of course, more of the tissue-removing element 3 may be exposed without departing from numerous aspects of the invention. Preferably, when the tissue-removing element 3 is in the cutting position, a longitudinal axis 28 of the tissue-removing element 3 is oriented at an attack angle 25 relative a longitudinal axis 9 of a leading portion of the catheter body 8.

Catheter 2 may have a maximum size of 3, 4, 5, 6, 7, 8, 9, 10, or 12 French (1, 1.3, 1.7, 2, 2.3, 2.7, 3, 3.3, or 4 mm) and may have a working length ranging of 20, 30, 40, 60, 80, 100, 120, 150, 180 or 210 cm depending on the requirements of the anatomical location in which use of the catheter is contemplated.

In the illustrated embodiment, the catheter 2 is moved distally through a vessel with the tissue-removing element 3 in the working or cutting position as described in further detail below. As the catheter 2 moves through the blood vessel, the tissue is cut by the tissue-removing element 3 and is directed into a tissue chamber 12 positioned distal to the tissue-removing element 3. The tissue chamber 12 may be somewhat elongate to accommodate the tissue that has been cut.

Referring to FIG. 3, the illustrated tissue-removing element 3 is moved proximally from the stored position so that a cam surface 14 on the tissue-removing element 4 engages a ramp 16 on the body 8 of the catheter 2. The interaction between the cam surface 14 and the ramp 16 causes the tissue-removing element 3 to move to the cutting position and also causes a tip 18 to deflect which tends to move the tissue-removing element 3 toward the tissue to be cut. The tissue-removing element 3 may be deployed in other ways without departing from the scope of the present invention.

The tissue-removing element 3 is coupled to a drive shaft 20 that extends through a lumen 21 in the catheter 2. The tissue-removing element 3 is rotated about an axis of rotation A in a rotational direction R when the drive shaft rotates about its longitudinal axis. The tissue-removing element 3 may be rotated at about 1 to 160,000 rpm in use but may be rotated at any other suitable speed depending upon the particular application. Other ways of driving rotation of the tissue-removing element 3 do not depart from the scope of the present invention.

Figure 4:
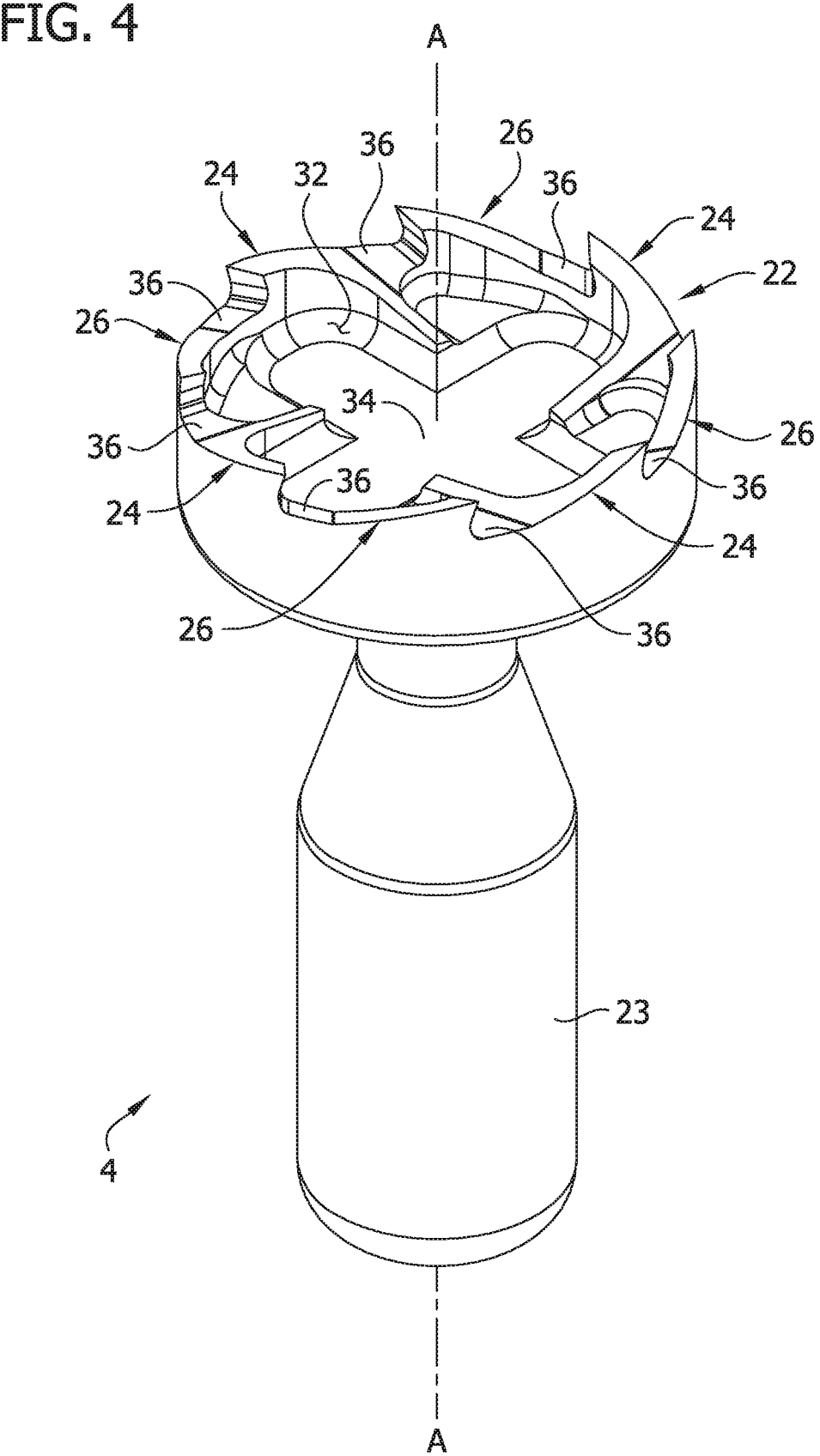
FIG. 4 is a perspective of the tissue-removing element.

Referring to FIG. 4, a first embodiment of a tissue-removing element of the present disclosure is generally indicated at reference numeral 4. The tissue-removing element has distal and proximal axial ends (broadly, "first and second axial ends"). The tissue-removing element 4 includes a tissue-removing head, generally indicated at reference numeral 22, at the distal axial end thereof. A stem 23 of the tissue-removing element 4 connects the tissue-removing element to the drive shaft 20. The tissue-removing head 22 comprises alternating primary and secondary tissue-removing components 24, 26, respectively, extending around the axis of rotation A. The primary tissue-removing components 24 are radially spaced from the axis of rotation A of the tissue-removing element 4 and angularly spaced from one another around the axis of rotation. Likewise, the secondary tissue-removing components 26 are radially spaced from the axis of rotation A and angularly spaced from one another around the axis of rotation. Each of the secondary tissue-removing components 26 is interposed between adjacent ones of the primary tissue-removing components 24. In the illustrated embodiment, the annular tissue-removing blade 22 comprises four primary tissue-removing components 24 and four secondary tissue-removing components 26 interleaved between the primary tissue-removing components. Though the illustrated embodiment uses four primary tissue-removing components 24 and four secondary tissue-removing components 26, it will be understood that any number of primary and secondary tissue-removing components can be used without departing from the scope of the invention. The primary and secondary tissue-removing components 24, 26 extend generally axially so that a radially central region of the tissue-removing element 4 at its distal end defines a recess 32 with a flat bottom surface 34. Gullets 36 are disposed between each adjacent primary tissue-removing component 24 and secondary tissue-removing component 26.

In the illustrated embodiment, the tissue-removing element 4 is integrally formed of one piece of material. Thus, the primary and secondary tissue-removing components 24, 26, respectively, are integrally formed of one piece of material. In other embodiments, it is contemplated that the tissue-removing element 4 can be a multi-piece assembly without departing from the scope of the invention. In one or more embodiments, the one-piece tissue-removing element 4 can be made from one of 465 stainless steel, 17-4 stainless steel, MP35N alloy, 35N LT alloy, titanium, and blends thereof. Other materials, such as other types of stainless steel, nickel, cobalt, chromium molybdenum, plastic, or combinations thereof, can also be used without departing from the scope of the invention.

Figure 5:
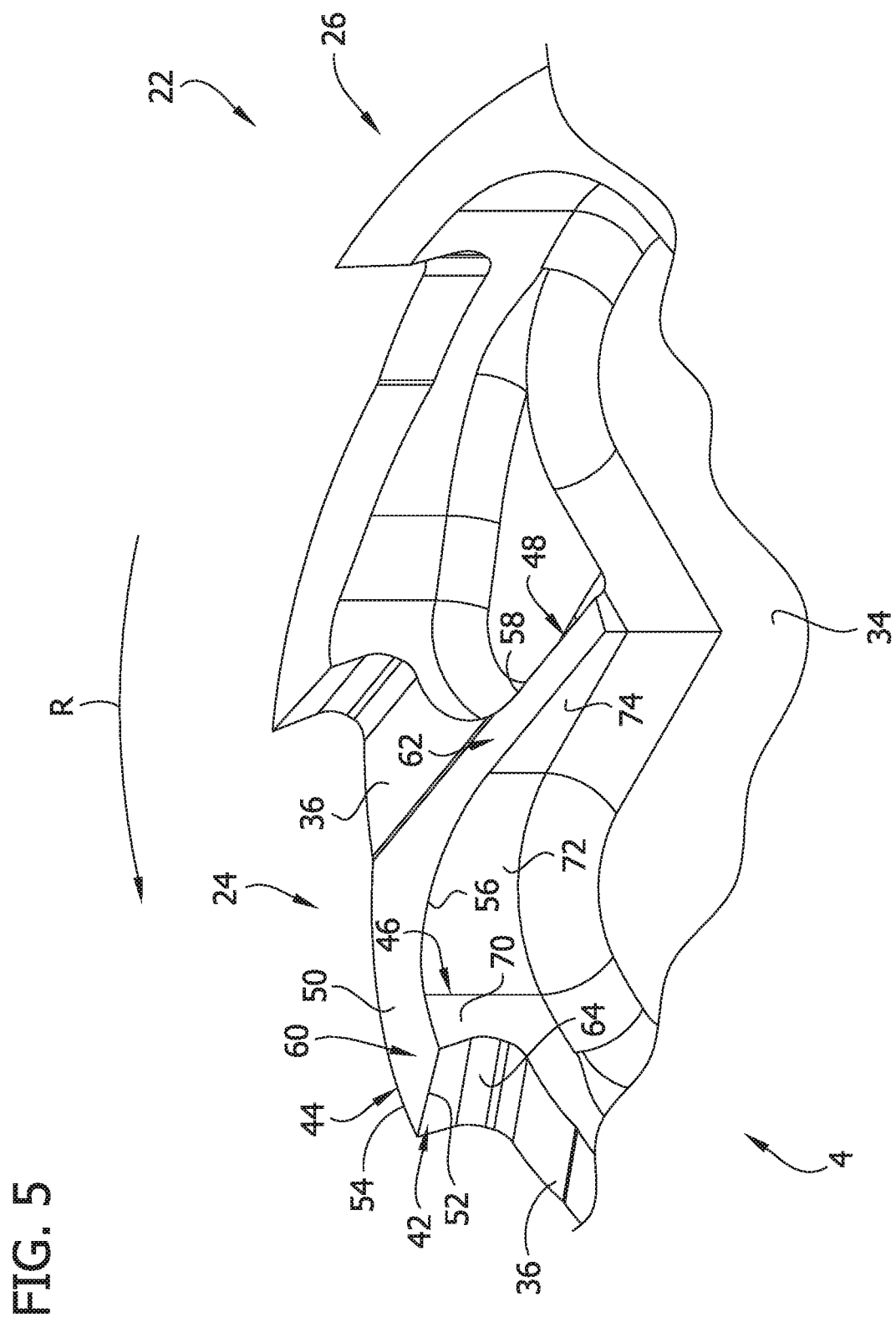
FIG. 5 is a fragmentary perspective of the tissue-removing element.

Referring to FIG. 5, each primary tissue-removing component 24 has a leading surface 42, a radially outer surface 44, a radially inner surface 46, and a trailing surface 48, each of which is indicated generally in the drawings and extends generally axially outward in the distal direction at the distal end of the tissue-removing element 4. The leading surface 42 is at the forward or leading end of the primary tissue-removing component 24 in the cutting direction R. An axial end surface 50 intersects each of the leading, radially outer, radially inner, and trailing surfaces 42, 44, 46, 48 at respective leading, radially outer, radially inner, and trailing edges 52, 54, 56, 58. The leading surface 42; the leading edge 52; and leading portions of the radially outer surface 44, the radially inner surface 46, the radially outer edge 54, and the radially inner edge 56 form a cutting tooth, generally indicated at 60. The trailing surface 48; the trailing edge 58; and trailing portions of the radially outer surface 44, the radially inner surface 46, the axial end surface 50, the radially outer edge 54, and the radially inner edge 56 form an inner shearing member, generally indicated at 62.

Each integrally formed cutting tooth 60 and inner shearing member 62 operate together to engage hard and soft tissue in a body lumen and shear tissue (e.g., plaque) from the luminal wall, and bluntly impact the tissue so as to break the tissue free from the luminal wall. The integrally formed cutting tooth 60 and inner shearing member 62 operate together to effectively remove multiple types of tissue from a body lumen by attacking the tissue in multiple different ways as the tissue-removing element 4 advances axially through the body lumen and rotates in the cutting direction. As will be discussed in greater detail below, the integrally formed cutting tooth 60 and inner shearing member 62 are preferably formed by removing material from a blank with a cutting implement.

Referring to FIGS. 4 and 5, each secondary tissue-removing component 26 also defines a cutting tooth (indicated by the same reference number 26). However, the secondary tissue-removing components 26 do not define inner shearing members 62. As explained in more detail below, the parts of the secondary cutting teeth 26 are substantially similar to the corresponding parts of the primary cutting teeth 60, other than the absence of the integrally formed inner shearing members.

Figure 6:
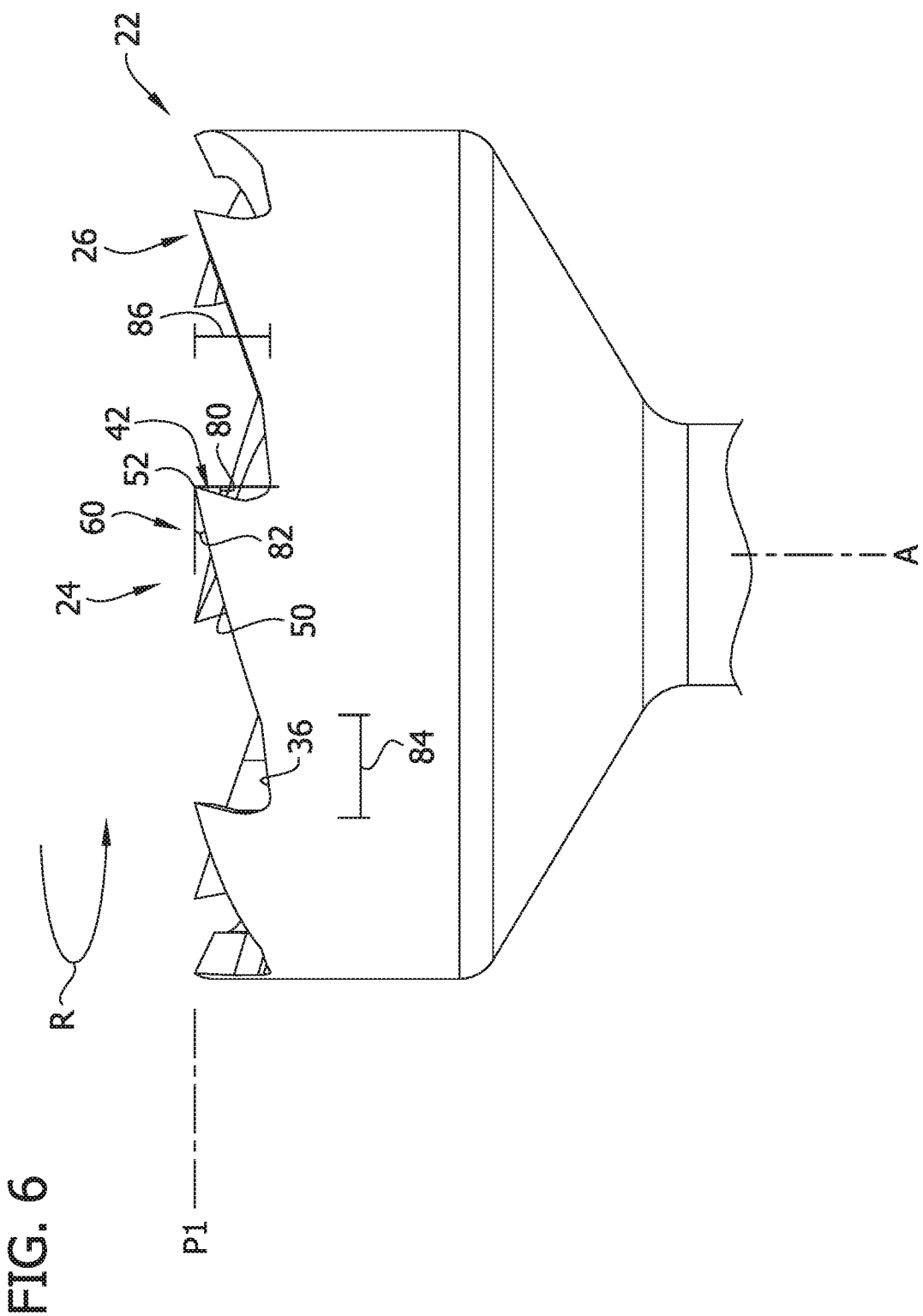
FIG. 6 is a fragmentary elevation of the tissue-removing element.

In the illustrated embodiment, as shown in FIG. 6, distal tips (e.g., the intersections of the leading edges 52 and the outer radially surfaces 44) of each of the primary and secondary cutting teeth 60, 26 define a cutting plane P1 oriented generally orthogonal to the axis of rotation A. Throughout the present disclosure, the cutting plane P1 of the tissue-removing element 4 is a plane in which the distal tips of at least two cutting components 24, 26 are positioned. It is also contemplated that in other embodiments the distal tips of some of the primary and secondary cutting teeth 60, 26 may be axially offset from the cutting plane P1 so that only selected ones define the cutting plane. Generally, the cutting plane P1 will be oriented generally orthogonal to the axis of rotation A of the tissue-removing element 4. However, it is contemplated that the cutting plane can be oriented at another angle with respect to the axis of rotation A without departing from the scope of the invention.

Reference is now made to one of the primary cutting teeth 60 with the understanding that the description set forth below applies equally to each of the primary cutting teeth. The primary cutting tooth 60 is adapted to cut tissue as the tissue-removing element 4 rotates to facilitate removal of soft tissue. Referring to FIG. 5, the leading surface 42 forming the primary cutting tooth 60 extends axially in the distal direction from the trailing end portion of the adjacent gullet 36 and radially between the radially outer surface 44 and radially inner surface 46. The leading surface 42 has an undercut 64 so that the leading edge 52 of the primary cutting tooth 60 is proud (i.e., leads in the cutting direction R) of at least a portion of the undercut. The radially outer surface 44 forming the primary cutting tooth 60 is contiguous with the generally cylindrically shaped radially outer surface of the tissue-removing head 22 of the tissue-removing element 4. The leading portion 70 of the radially inner surface 46 forming the primary cutting tooth 60 is generally planar. The radially inner surface 46 extends axially in the distal direction from the flat bottom surface 34 of the recess 32 toward the radially inner edge 56. A distal portion of the radially inner surface 46 is oriented substantially perpendicular to the flat bottom surface 34 of the recess 32 and a proximal portion of the radially inner surface forms a radius between the distal portion thereof and the flat bottom surface.

Referring to FIG. 6, the leading surface 42 forming the primary cutting tooth 60 defines a rake angle 80 of the tooth. When viewed from a side-elevation as in FIG. 6, the rake angle 80 of the primary cutting tooth 60 is measured as the angle between the leading surface 42 relative to a line orthogonal to the cutting plane P1. Each cutting tooth 60 may have a positive rake angle 80 because the leading surface 42 of the cutting tooth trails the line perpendicular to the cutting plane P1 in the cutting direction R. The positive rake angle 80 of the primary cutting tooth 60 causes the leading surface 42 of the tooth to hook and pull soft tissue as it rotates in the cutting direction R. This strong engagement between the primary cutting tooth 60 and soft tissue helps the tissue-removing element 4 slice into soft tissue and pull it away from the body lumen wall. In addition, due to the positive rake angle 80, when the primary cutting tooth 60 engages hard tissue as it rotates in the cutting direction R, it imparts a high degree of stress on the tissue because the force imparted on the tissue is concentrated at the leading edge 52 forming the tooth. In one or more embodiments, the rake angle 80 of the primary cutting tooth 60 may be from about +5° to about +35°. However, it will be understood that other rake angles can also be used without departing from the scope of the invention.

Referring still to FIG. 6, in the illustrated embodiment, the primary cutting tooth 60 has a relief angle 82, which is the angle between the cutting plane P1 and the portion of the axial end surface 50 defining the cutting tooth. In one or more embodiments, the tooth relief angle 82 is chosen to maximize a width 84 of the gullet 36 without compromising the robustness of the primary cutting tooth 60 or the operation of the catheter 2. An excessively large relief angle 82 may remove too much material from the leading portion of the primary cutting tooth 60, which may weaken the structure thereof. In addition, an excessively large relief angle 82 may cause the primary cutting tooth 60 to engage tissue at a depth which requires the drive shaft 20 to produce a large amount of torque to effectively remove the tissue. This may cause the catheter 2 to fail (e.g., a broken driveshaft, stalled motor, etc.) or the cutting tooth 60 to disengage from the tissue rather than break through it as the tissue-removing element 4 rotates in the cutting direction R. If the relief angle for the cutting tooth 60 is too small, the tissue-removing element 9 will not advance axially through tissue in the lumen at the desired rate. When the tissue-removing element 4 is formed by removing material from a generally cylindrical blank (as explained below), a larger gullet width 84 (such as shown in FIG. 6) allows large cutting implements to be passed over the gullet and used to cut away material of the blank inside the recess 32. In one or more examples, the relief angle 82 may be about 14°. However, it will be understood that other relief angles can also be used without departing from the scope of the invention.

As shown in FIG. 6, a tooth height 86 of the primary cutting tooth 60 is the dimension in the axial direction between the distal tip of the primary cutting tooth and the proximal-most point of the cutting tooth, where it begins to extend in the axially distal direction away from the adjacent, leading gullet 36. In the illustrated embodiment, the tooth height 86 may be about 0.005 inches; however, other tooth heights can also be used without departing from the scope of the invention.

Figure 7:
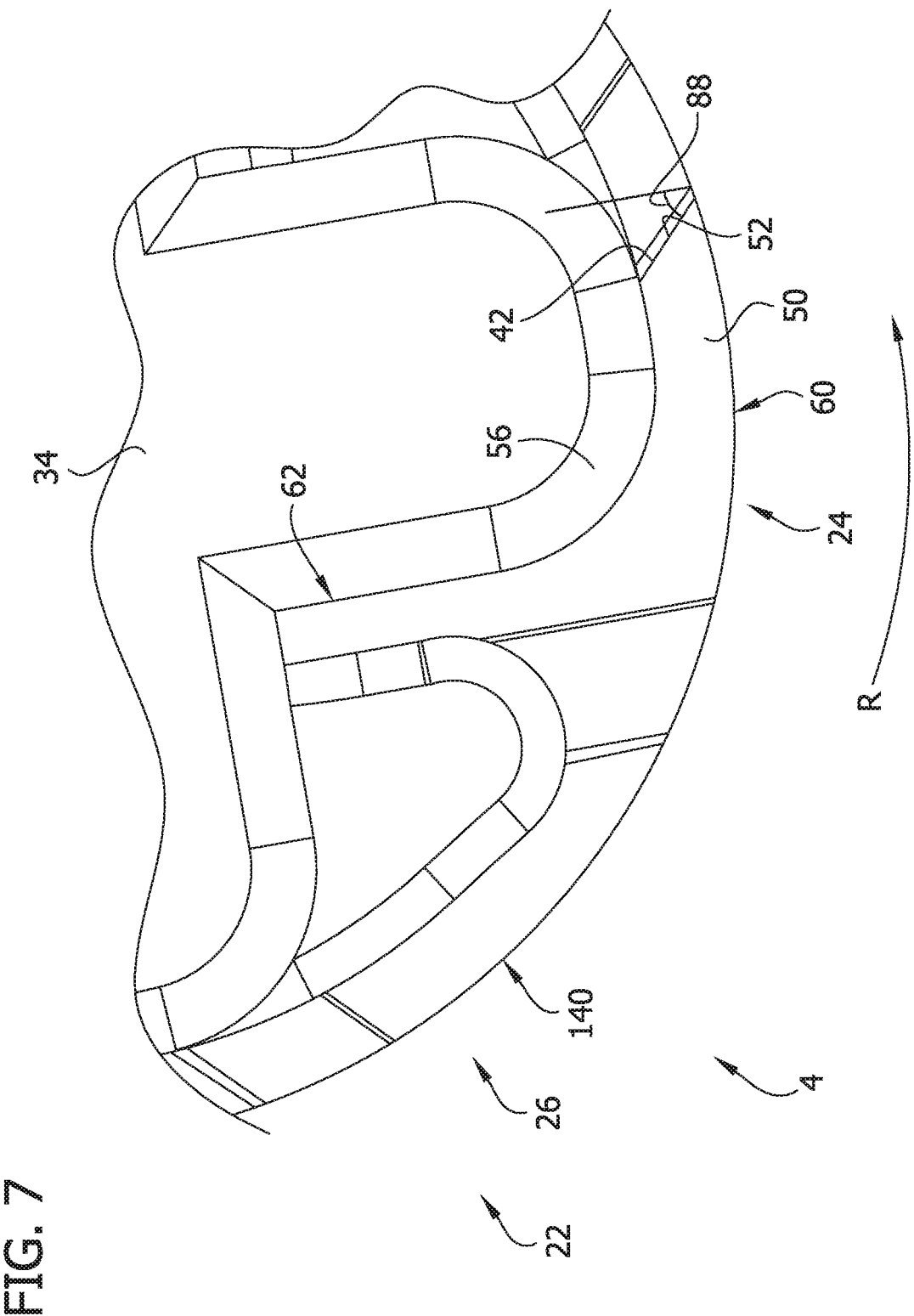
FIG. 7 is a fragmentary top plan view of the tissue-removing element.

Referring to FIG. 7, the leading edge 52 forming the primary tooth 60 defines a fleam angle 88 of the cutting tooth 60. When the tissue-removing element 4 is viewed from the distal axial end as shown in FIG. 7, the fleam angle 88 of the primary cutting tooth 60 is the angle between the leading edge 52 and a line perpendicular to a line tangent to the perimeter of the annular tissue-removing head 22. A greater fleam angle 88 creates a sharper cutting tooth 60 that slices through soft and hard tissue more efficiently. In addition, when the fleam angle 88 is greater than 0°, the leading surface 42 of a cutting tooth 60 engages tissue at an angle, which causes the tissue to shear radially inwardly. By comparison, the leading surface of a cutting tooth with a fleam angle of 0° (not shown) engages tissue at a substantially normal angle relative the linear direction of its motion, which may not cause shearing. The improved tissue-removing properties of the primary cutting tooth 60 with a non-zero fleam angle 88 are balanced against the robustness of the leading portion of the cutting tooth. A larger fleam angle 88 results in less material at the leading portion of the primary cutting tooth 60, which may adversely affect robustness. In one or more embodiments the fleam angle 88 is greater than 0°, such as from about 1° to about 60°.

Figure 8:
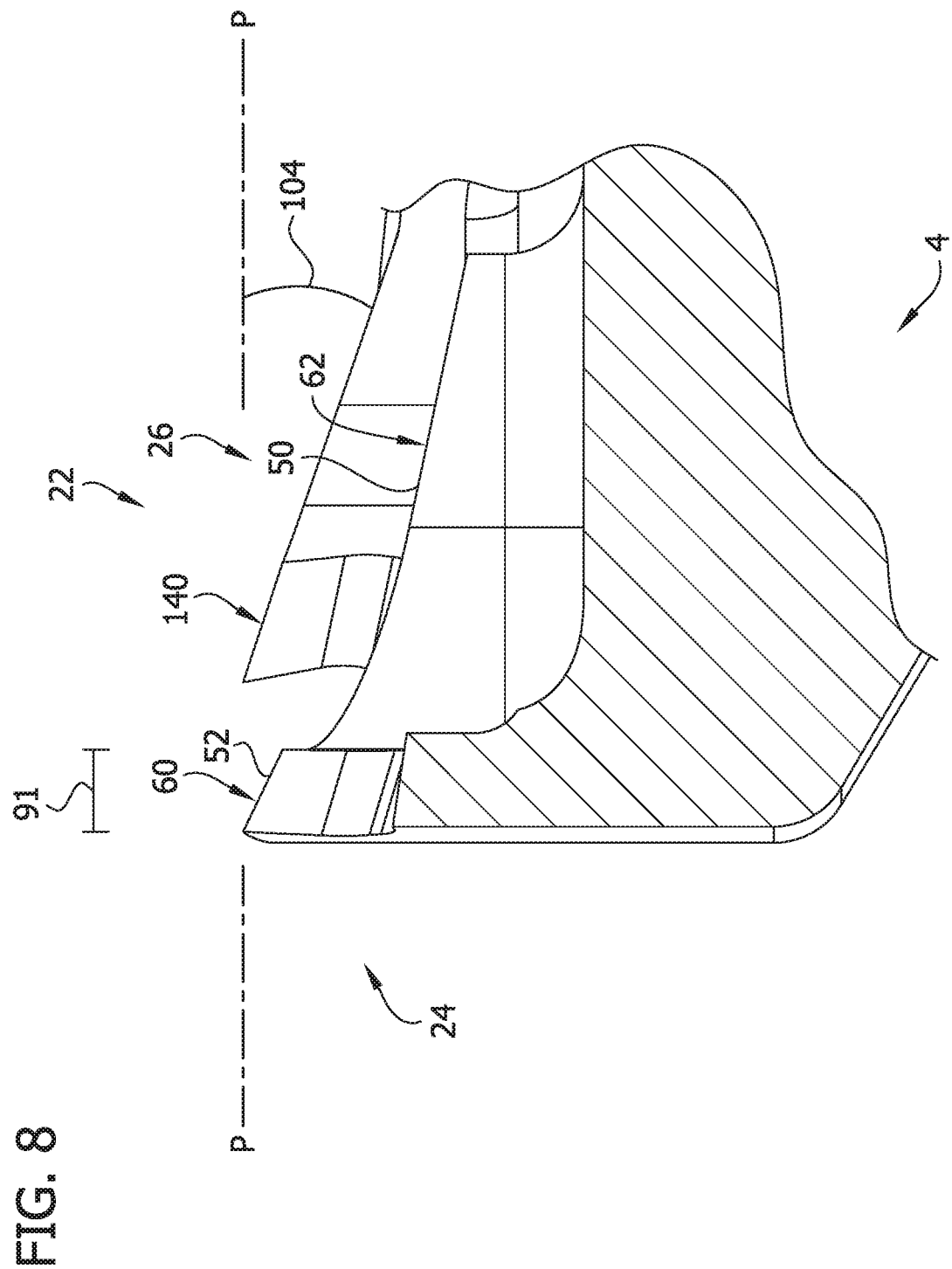
FIG. 8 is fragmentary section of the tissue-removing element.

As shown in FIG. 8, the primary cutting tooth 60 has a tooth thickness 91 measured in the radial direction between the radially inner and outer surfaces 46, 44. When the cutting tooth 60 cuts through hard tissue, it makes a kerf in the tissue having a width that substantially corresponds to the tooth thickness 91. When the cutting tooth 60 cuts through soft tissue, it cleaves, slices, or shears the tissue, creating a crevice or other deformation that substantially corresponds in thickness with the tooth thickness 91. The tooth thickness 91 affects the robustness of the cutting tooth 60 and its engagement with hard and soft tissue. A greater tooth thickness 91 improves robustness because the primary cutting tooth 60 comprises more material, which enhances strength. However, a lesser tooth thickness 91 allows the cutting tooth 60 to pass with less resistance through tissue as it rotates in the cutting direction R. In one or more embodiments, the thickness 91 of the primary cutting tooth 60 is substantially constant along its height 86 and may measure from about 0.0005 inches to about 0.0100 inches, and in one embodiment, about 0.0035 inches. In one or more embodiments, the thickness 91 of each cutting tooth 60 may be from about 1% to about 50% of the outer radius of the tissue-removing head 22. Other tooth thicknesses can also be used without departing from the scope of the invention. In the illustrated embodiment, the thickness of the portion of the cutting head 22 that trails the inner shearing member 62 is thicker than the thickness 91 of the cutting tooth 60 so that a large cutting implement can be used to form the radially inner surfaces of the trailing primary and secondary tissue-removing components 24, 26.

In the illustrated embodiment, a section taken along the height 86 of the primary cutting tooth 60 has a generally trapezoidal shape with sides that are generally parallel. In other embodiments, a section taken along the height 86 of the primary cutting tooth 60 may have a generally wedge shape. A cutting tooth with a wedge sectional shape has sides that are oriented at an angle relative to one another such that the cutting tooth is narrower at one axial end than the other axial end. A wedge sectional shape tends to cause tissue to bend radially inward toward the axis of rotation A of the tissue-removing element 4 as the catheter 2 is advanced in the axial direction and the tissue-removing element rotates about its axis of rotation A. By comparison, the illustrated cutting tooth 60, with its trapezoidal sectional shape, tends to bite through hard tissue rather than bend the tissue.

Reference is now made to one of the inner shearing members 62, with the understanding that the description set forth below applies equally to each of the inner shearing members. Referring to FIG. 5, the inner shearing member 62 is adapted to impact tissue and shear it radially inwardly as the tissue-removing element 4 rotates to facilitate removal of hard tissue. The radially inner surface 46 has an arcuate portion 72 that curves radially inward relative to the axis of rotation A, away from the radially outer surface 44 and toward a trailing portion 74 of the radially inner surface, forming the inner shearing member 62. The trailing portion 74 of the radially inner surface 46 extends radially inward relative to the axis of rotation A in a direction generally transverse to the perimeter of the annular tissue-removing head 22. The axial end surface 50 and the arcuate and trailing portions 72, 74 (along with the trailing surface 48) form the inner shearing member 62. The axial end surface 50 forming the inner shearing member 62 is substantially planar and lies in a different plane than the trailing, adjacent gullet 36. Thus, the axial end surface 50 forms an angle less than 180° relative the gullet 36.

In the illustrated embodiment, the arcuate portion 72 of the radially inner surface 46 of each primary tissue-removing component 24 is configured to shear tissue radially inward with respect to the tissue-removing element 4. The trailing portion 74, which acts as the impact surface of the inner shearing member 62, is configured to impact tissue at an obtuse angle to further shear the tissue radially inwardly as the tissue-removing element 4 rotates in the cutting direction R. The arcuate portion 72 has a radius of curvature 92, and the trailing portion 74 has a length 94 (See FIG. 9). The dimensions for the radius of curvature 92 and the length 94 affect the shearing action of the arcuate portion 72 and the impacting action of the trailing portion 74 and are limited by the available space for the inner shearing member 62. In the illustrated embodiment, the radius of curvature 92 may be about 0.0085 in. In one or more embodiments, the radius of curvature 92 of the arcuate portion 72 of the inner shearing member 62 may be from about 1% to about 50% of the radius of the outer tissue-removing blade 22. Likewise, in one or more embodiments, the length 94 of the impact surface of an inner shearing member (e.g., the trailing portion 74 of the radially inner surface 46) may be from about 1% to about 75% of the radius of the outer tissue-removing blade 22.

Figure 9:
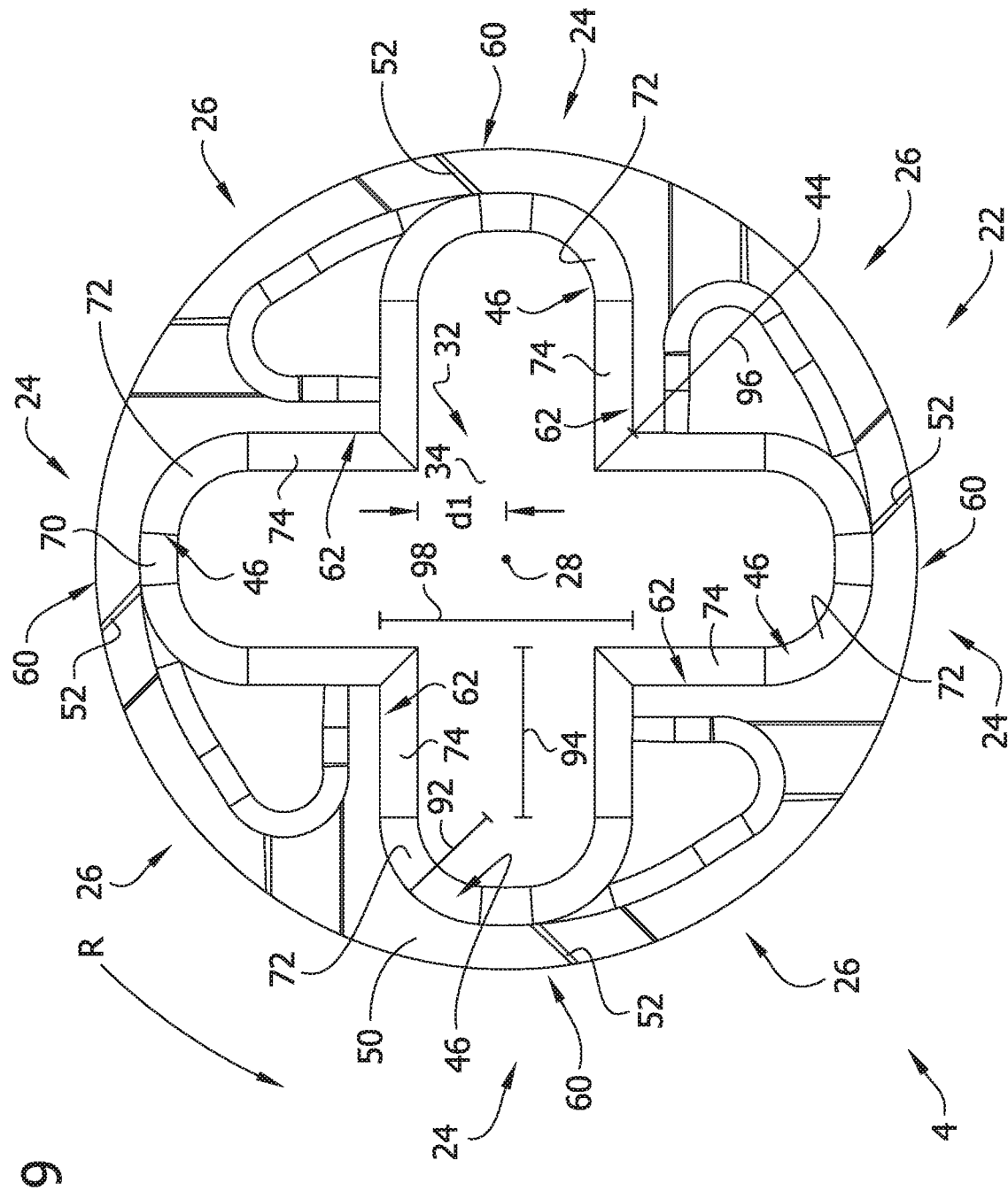
FIG. 9 is a top plan view of the tissue-removing element.

Referring to FIG. 9, in the illustrated embodiment, the four inner shearing members 62 are formed in a crosscut pattern (i.e., the flat bottom surface 34 of the recess 32 is cross-shaped). The crosscut pattern enables the inner shearing members 62 to be machined relatively easily using a single cutting implement at a fixed axial cutting depth. A crosscut width 98 measures the distance between the trailing end of one inner shearing member 62 and the impact surface (i.e., the trailing portion 74 of the radially inner surface 46) of the adjacent, trailing inner shearing member. The crosscut width 98 is preferably chosen to optimize the angle of impact of the inner shearing member 62. When the impact surface 74 is in line with a radius of the tissue-removing head 22, the inner shearing member impacts hard tissue at an impact angle perpendicular to the impact surface, which causes braking of the rotation of the tissue-removing element 4 and reduces tissue-removal efficiency. In the illustrated embodiment, the plane of the impact surface 74 of each inner shearing member 62 is offset a distance d1 (e.g., about 0.010 inches) from the axis of rotation A in a direction perpendicular to the plane. As a result, the impact surface 74 of each inner shearing member 62 impacts hard tissue at an obtuse impact angle. This reduces the tendency of impacts between one of the inner shearing members 62 and hard tissue to cause braking of the rotation of tissue-removing element 4. In addition, it enables impacts between the tissue and the impact surface 74 to shear the tissue away from the body lumen wall. As compared with a purely blunt impact that does not tend to shear the tissue, the shearing caused by the impact surface is believed to improve the efficiency with which the tissue-removing element 4 fractures hard tissue.

Referring still to FIG. 9, each inner shearing member 62 has a radial length 96 that is measured as the distance between the radially outer surface 44 of the tissue-removing head 22 and the radially innermost point of the inner shearing member 62 along an imaginary line that passes through both the axis of rotation A and the innermost point of the inner shearing member 62 in a plane parallel to the cutting plane P1. To maximize the capability of the inner shearing member 62 to impact tissue at any radial position in the body lumen, the radial length 96 may be equal to the radius of the tissue-removing head 22. However, to facilitate the crosscut pattern by which the inner shearing members 62 are manufactured, the inner shearing member radial length 96 is preferably less than the radius of the tissue-removing head 22. In one or more embodiments, the inner shearing member radial length 96 may be from about 10% to about 80% of the radius of the tissue-removing head 22. In the illustrated embodiment, the inner shearing member radial length 96 may be about 0.018 in. In one or more embodiments, the breaker radial length 96 is sized so that, as the cutting element 4 rotates in the deployed position, the primary tissue-removing component 24 spans the entire distance between the cutter opening 6 and the wall of the body lumen. This arrangement maximizes the engagement between the inner sharing member 62 and the tissue. Alternatively, the breaker radial length 96 can be sized so that, as the cutting element 4 rotates in the deployed position, the primary tissue-removing component 24 spans only a radially outer portion of the distance between the cutter opening 6 and the wall of the body lumen. This arrangement allows the flat surface 34 of the recessed portion of the cutting head 22 to redirect cut tissue toward the tissue chamber 12.

Figure 10:
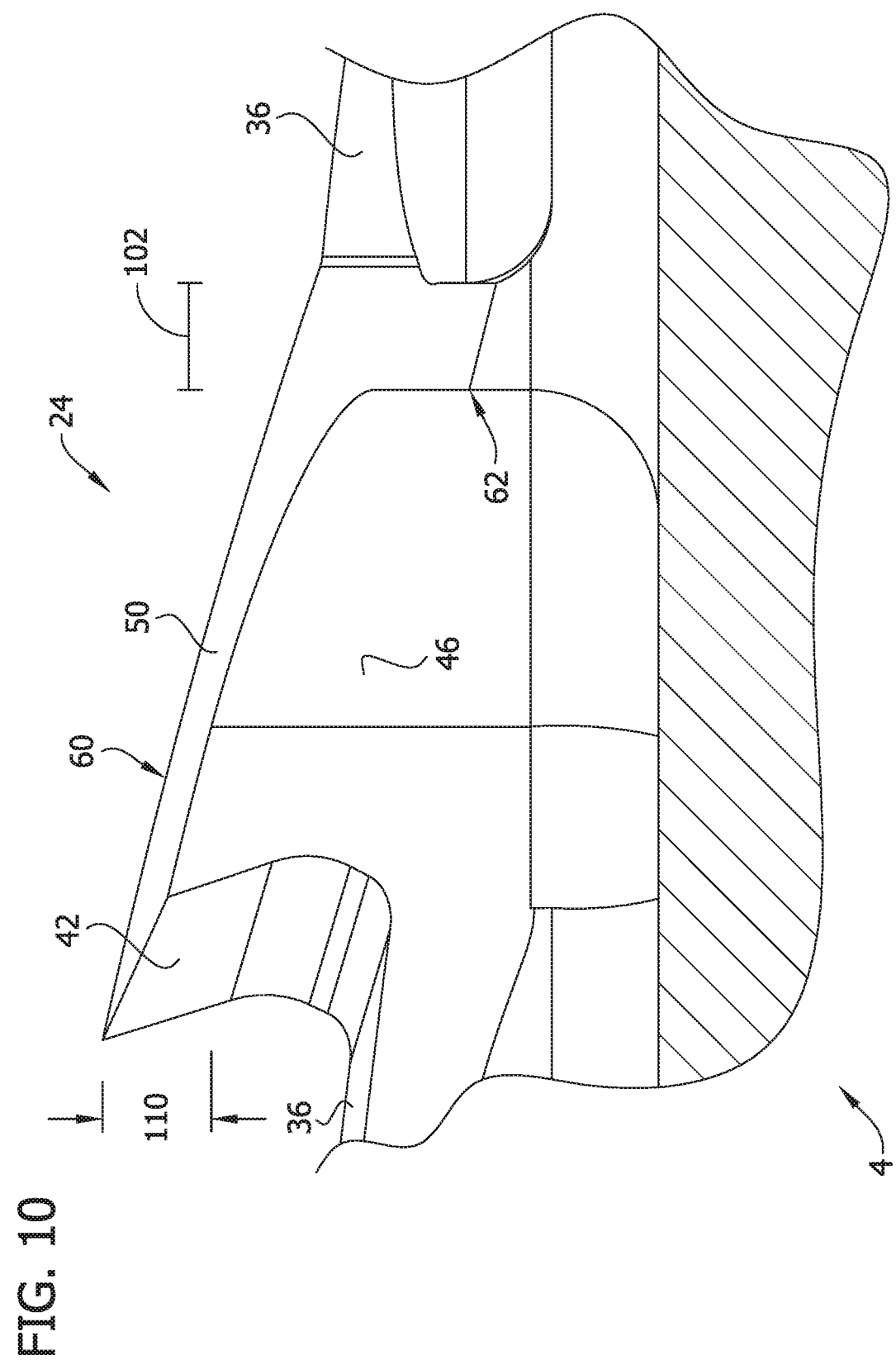
FIG. 10 is another fragmentary section of the tissue-removing element.

As shown in FIG. 10, the inner shearing member 62 has an inner shearing member thickness 102. The inner shearing member thickness 102 affects the gullet width 84 (FIG. 6) and the robustness of the inner shearing member 62. The inner shearing member thickness 102 also affects the size of cutting implement used to form the radially inner surfaces of the trailing primary and secondary cutting elements 24, 26. The gullet width 84 is preferably sufficiently small so that the planar axial end surface 50 can extend continuously from the cutting tooth 60 through the entire thickness 102 of the inner shearing member 62. In the illustrated embodiment, the inner shearing member thickness 102 may be about 0.0025 in or about 8% of the outer radius of the tissue-removing element 4. In one or more embodiments, the inner shearing member thickness may be from about 1% to about 30% of the outer radius of the tissue-removing element 4. In other embodiments, the inner shearing member thickness 102 can be other dimensions without departing from the scope of the invention.

Figure 11:
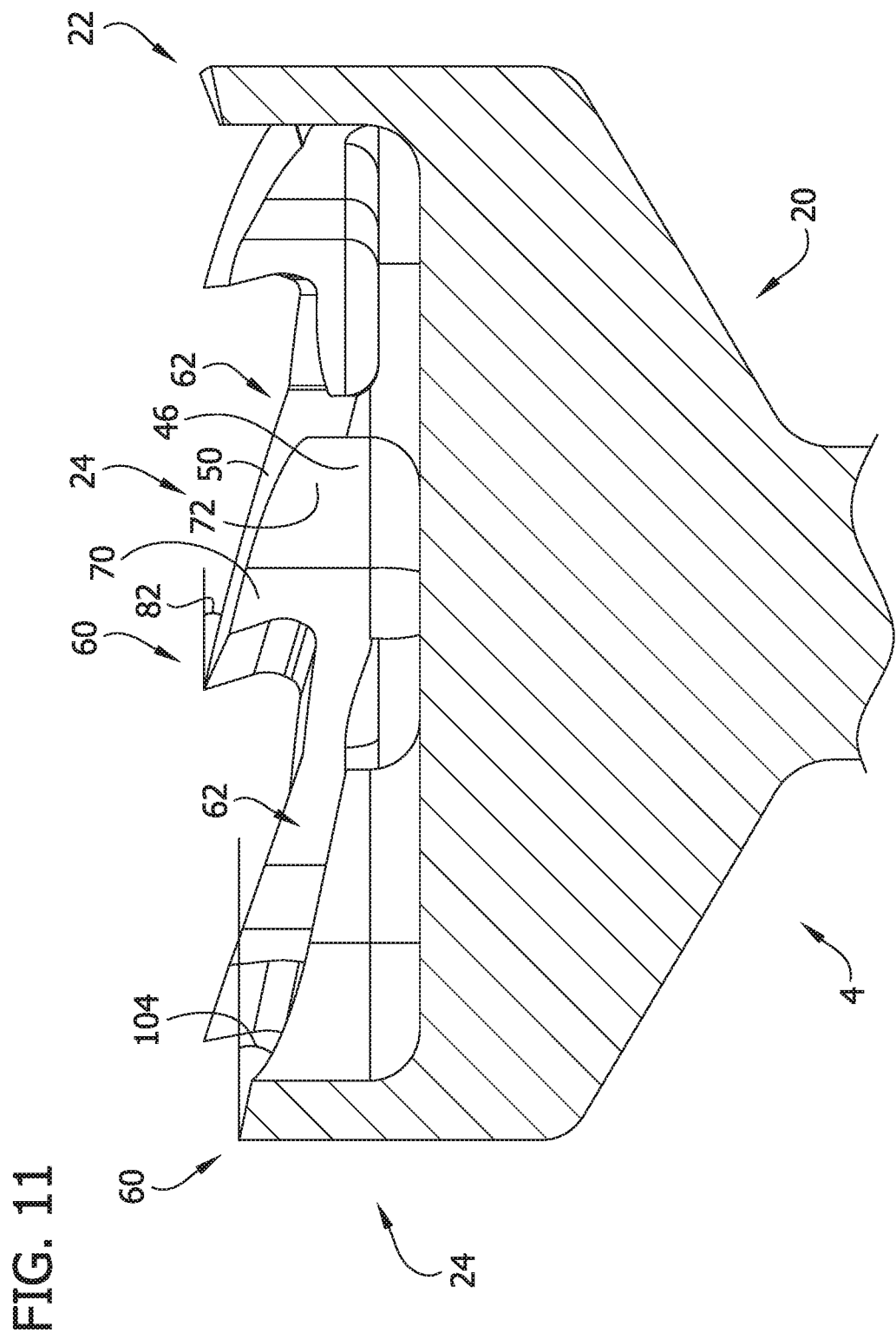
FIG. 11 is another fragmentary section of the tissue-removing element.

Referring to FIGS. 8 and 11, the axial end surface 50 of each primary tissue-removing component 24 is a continuous planar surface that spans the cutting tooth 60 and the inner shearing member 62. The axial end 50 and the leading edge 52 of the cutting tooth 60 may be tilted or sloped inward from the radially outer surface 44 to the radially inner surface 46 relative to the cutting plane P1 at a tilt angle 104. Thus, the axial end surface 50 is oriented at the relief angle 82 and the tilt angle 104. For each primary tissue-removing component 24, the axial end surface 50 of the cutting tooth 60 and the inner shearing member 62 can be formed together by selectively orienting a cutting implement at a desired angle relative the axis of rotation A of the tissue-removing element 4 and removing material therefrom with the cutting implement oriented at the desired angle, without changing the angle of the cutting implement relative the axis of rotation.

Since the axial end surface 50 is a continuous planar surface that spans the cutting tooth 60 and the inner shearing member 62, the axial end surface of the inner shearing member 62 is oriented at the tilt angle 104 with respect to the cutting plane P1. As discussed above, the tissue-removing element 4 extends through the tissue-removing element window 6 of the catheter 2 at an attack angle 25 relative the longitudinal axis of the distal portion of the catheter body 8 (See FIG. 3). Preferably, the tilt angle 104 of the axial end surface 50 of each inner shearing member 62 is operable to permit the inner shearing member to engage tissue. If the tilt angle 104 is too low, engagement between the inner shearing member 62 and tissue can cause the tissue-removing element 4 to move away from the tissue as the catheter 2 advances in the axial direction. However, if the tilt angle 104 of the inner shearing member 62 is too high, the inner shearing member of the cutting element 4 can advance toward the tissue in the body lumen with such high force that excessive friction between the tissue and the cutting element is created. Preferably the tilt angle 104 is chosen to inhibit the tissue-removing element 4 from moving away from the tissue and to likewise inhibit the tissue-removing element from advancing toward the tissue with such high force as to create excessive friction between the tissue-removing element and the tissue. In preferred embodiments, the tilt angle is greater than or equal to the attack angle 25.

As shown in FIG. 10, each of the primary tissue-removing components 24 has an inner shearing member depth 110 measured as the axial distance between the distal-most end of the cutting tooth 60 and the distal-most end of the inner shearing member 62. In the illustrated embodiment, the distal-most end of the cutting tooth 60 is the distal tip of the primary tissue-removing component 24 at the radially outer surface 44. The distal-most end of the inner shearing member 62 is the distal end (and leading end) of the arcuate portion 72 of the radially inner surface 46. Because the trapezoidal shaped cutting tooth 60 bites through hard tissue in the body lumen rather than bending the tissue radially inward toward the axis of rotation A, an inner shearing member depth 110 greater than zero does not hinder the cutting efficiency of the primary tissue-removing components 24. By comparison, when a wedge-shaped kerf causes tissue to bend radially inward, the bent tissue increases the friction on the tissue-removing element as it rotates and pushes back against the axial advancement of the catheter 2 through the body lumen, thereby hindering cutting efficiency. As a result, to maximize cutting efficiency, it is preferable to minimize the inner shearing member depth 110 with a cutting tooth that has a wedge-shaped cross-sectional shape. However, due to other design factors and manufacturability considerations, it can be preferable to have a larger inner shearing member depth 110. In the illustrated embodiment, the inner shearing member depth 110 may be about 0.0023 in. Other inner shearing member depths can also be used without departing from the scope of the invention.

A minimum tooth height 111 also affects cutter efficiency and engagement. In the illustrated embodiment, the minimum tooth height 111 is measured as the axial distance between the distal tip of the radially inner surface 46 forming the cutting tooth 60 and the distal-most end of the inner shearing member 62. For cutting teeth that create a kerf in hard tissue like the cutting tooth 60, the maximum tooth height 111 is believed to affect the ability of the cutting head 22 to stay engaged in tissue as it rotates in the body lumen. If the minimum tooth height 111 is too small, the tooth 60 will create a shallow kerf in the tissue, and the trailing cutting teeth 26, 60 will have difficulty remaining radially aligned with the kerf. If the minimum tooth height is too great, the cutting tooth 60 will engage too deeply in the tissue, which can hinder operation of the catheter as discussed above.

Figure 12:
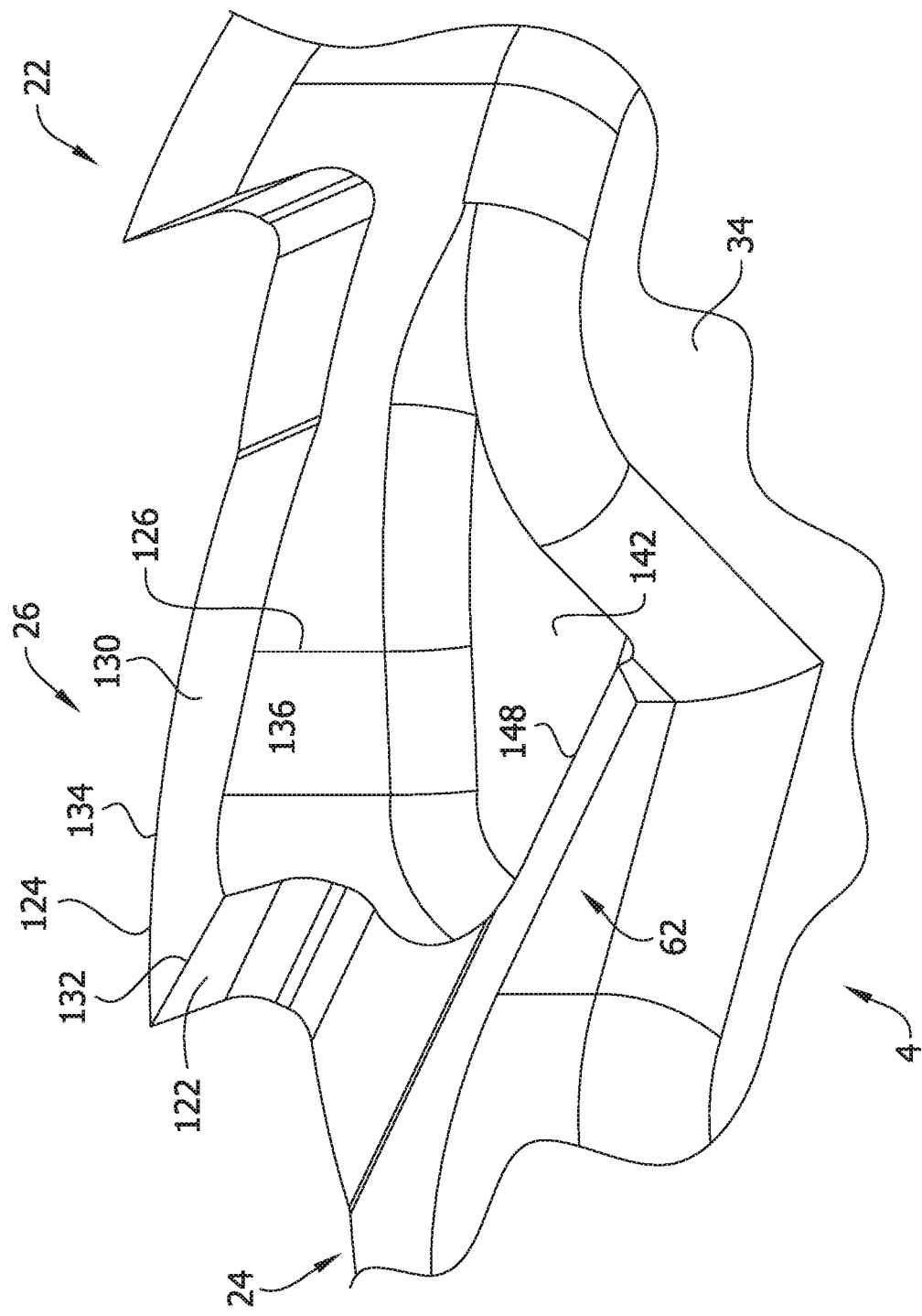
FIG. 12 is another fragmentary perspective of the tissue-removing element.

Referring to FIG. 12, each of the secondary tissue-removing components 26 (defining the secondary cutting teeth indicated by the same reference numeral 26) has a leading surface 122, a radially outer surface 124, and a radially inner surface 126 extending generally axially. In use, the leading surface 122 is at the forward end of the secondary tissue-removing component 26 as the tissue-removing element 4 rotates in the cutting direction R. An axial end surface 130 intersects each of the leading, radially outer, and radially inner surfaces 122, 124, 126 at respective leading, radially outer, and radially inner edges, 132, 134, 136. The leading, radially outer, radially inner, and axial end surfaces 122, 124, 126, 130 and leading, radially outer, and radially inner edges 132, 134, 134 define the secondary cutting tooth 26. An axially raised portion 142 extends axially in the distal direction between the trailing surface 148 of a primary tissue-removing component 24 and an adjacent, trailing secondary tissue-removing component 26. The raised portion 142 provides additional support and strength for the inner shearing member 62 of the primary tissue-removing component 124. However, being spaced apart proximally from the trailing edge 48 of the inner shearing member, the raised portion 142 also provides relief for tissue passing over the inner shearing member. The shallower depth of the raised portion 142 relative the flat surface 34 enables the radially inner surface of the gullet 36 to be machined more efficiently.

In the illustrated embodiment, the secondary cutting teeth 26 have rake angles, relief angles, tooth heights, fleam angles, and cross-sectional shapes that generally match those of the primary cutting teeth 60. As a result the same cutting implement(s) used to form the primary cutting teeth 60 can also be used to form the secondary cutting teeth 26. The secondary cutting teeth 60 improve the engagement of the cutting element 4 by increasing the surface area that is contacting the tissue at any given time (e.g., rather than a single primary tissue-removing component contacting the tissue, a primary tissue-removing component and portions of one or more secondary tissue-removing components might contact the tissue at the same time). In addition, the secondary cutting teeth 26 engage tissue in a body lumen in the same way as the primary cutting teeth 60 as the catheter 2 advances axially therein and the tissue-removing element 4 rotates in the cutting direction R. Although the illustrated secondary cutting teeth 26 have substantially the same geometry as the primary cutting teeth 60, the rake angle, relief angle, tooth height, fleam angle, and/or cross-section shape of the secondary cutting teeth could also be different than the primary cutting teeth without departing from the scope of the invention.

In an exemplary method of making the tissue-removing element 4, the tissue-removing element can be formed by removing material from a blank comprising a single piece of material using one or more cutting implements. In one or more embodiments, a blank comprises a generally cylindrical body of material with opposite first and second axial ends and an axis extending between the axial ends. In certain embodiments, only an axial end portion at the first axial end of the blank, which corresponds with the distal end of the tissue-removing element 4, is cylindrical. Thus, the blank can be preformed to have the shape of the proximal end portion of the tissue-removing element 4 or can be machined to form the shape of the proximal end portion of the tissue-removing element 4 as part of a method of making a tissue-removing element without departing from the scope of the invention.

In one method of making a tissue-removing element, a cutting implement, such as a milling cutter of a multi-axis mill or Swiss machine, removes material from the blank to form the primary cutting teeth 60 of the primary tissue-removing components 24 and likewise removes material from the blank to form the inner shearing member 62 of the primary tissue-removing components. For each primary tissue-removing component 24, the cutting implement preferably forms portions of the primary cutting tooth 60 and inner shearing member 62 simultaneously (i.e., in the course of a single pass of the cutting implement along a cutting path). A cutting implement preferably removes material from the blank to form a leading surface 42, radially inner surface 46, and contiguous axial end surface 50 to form one of the primary cutting teeth 60 and the corresponding inner shearing member 62. A cutting implement also removes material from the blank to form the gullets 36, the secondary tissue-removing components 26, and the recess 32.

In one or more embodiments, a single cutting implement is used to form the radially inner surface 46 forming the cutting tooth 60 and inner shearing member 62 of each primary tissue-removing component 24. For example, the radially inner surface 42 of the cutting tooth 60 and the inner shearing member 62 of each primary tissue-removing component 24—including the leading portion 70, the arcuate portion 72, and the trailing portion 74 of the radially inner surface—is formed in a single, continuous pass of the cutting implement along a cutting path oriented parallel to the axially extending surface portion of the radially inner surface 46. This single continuous pass of the cutting implement can, for example, comprise a finishing pass of the cutting implement after the bulk of the blank material adjacent the radially inner surface 46 has already been removed, or it can comprise an initial pass of the cutting implement before the radially inner surface has been otherwise formed. Likewise, in one or more embodiments, the flat bottom surface 34 of the recess 32 is formed using the same cutting implement as is used to form the radially inner surfaces 46 of the primary tissue-removing components 24.

In certain embodiments, a cutting implement oriented at a selected angle relative the axis of rotation A and cutting plane P removes material from the blank to form the axial end surface 50 of each cutting tooth 60 and inner shearing member 62 of a corresponding primary tissue-removing component 24. The selected angle of the cutting implement is chosen so a material-removal plane thereof is co-located with the axial end surface 50 of the cutting tooth 60. Preferably, the cutting implement performs one or more operations (i.e., passes of the cutting implement along a cutting path) with the cutting implement oriented at the selected angle relative the axis of rotation A and cutting plane P. The orientation of the cutting implement at the selected angle does not change for forming the axial end surface 50 of the cutting tooth 60 or inner shearing member 62. In certain embodiments, after the axial end surface 50 of one of the primary tissue-removing components 24 is formed, the blank is rotated a quarter-turn about its longitudinal axis and the cutting implement performs the same operations to remove material from the blank to form the axial end surface of an adjacent primary tissue-removing component. Additionally or in the alternative, the blank can be rotated one-eighth of one turn to form the axial end surface 130 of the secondary cutting tooth 26, which in the illustrated embodiment has the same relief angle and tilt angle as the primary tissue-removing component 24. The steps of rotating the blank and using the cutting implement in the selected orientation to perform the same operations is repeated two more times until the axial end surfaces 50, 130 of each of the primary tissue-removing components 24 and, optionally, the secondary tissue-removing components 26 are formed.

In an exemplary method of using the catheter 2 to remove tissue from a body lumen will now be described. A user inserts the catheter 2 into the body lumen (such as by using a guidewire), positions the tissue-removing element 4 in the deployed position, and rotates the tissue-removing element in the cutting direction R as the catheter advances axially through the lumen. Each primary tissue-removing element 24 engages and removes tissue (e.g., plaque) from the body lumen as it rotates about its rotation axis A and advances axially through the lumen. With respect to one of the primary tissue-removing components, the primary cutting tooth 60 of one of the primary tissue-removing components 24 engages the tissue first, before the corresponding inner shearing member 62, since it is the leading portion of the primary tissue-removing component. As the tissue-removing element 4 rotates in the cutting direction R, the leading surface 42 engages the tissue and shears it radially inward, toward the axis of rotation A. As the catheter 2 advances axially (e.g., distally) in the body lumen, the cutting tooth 60 bites through hard tissue, removing some of the tissue from a rectangular or trapezoidal kerf. In addition, the cutting tooth 60 slices through soft tissue, cleaving it radially inward of the luminal wall. Tissue that is positioned radially inward of the kerf rides along the radially inner surface 46 of the primary tissue-removing component 24. When the arcuate portion 72 of the radially inner surface 46 defining the corresponding inner shearing member 62 engages the tissue, it shears the tissue radially inward. Depending on the material properties of the tissue, the tissue might fracture upon engaging the arcuate portion 72 or curl radially inwardly in response to the shearing. The trailing portion 74 of the radially inner surface 46 defining the inner shearing member 62 impacts any tissue located at a sufficiently radially inward position for engagement therewith at an obtuse angle, which causes further shearing of the tissue. Preferably, the impact between the trailing portion 74 of the radially inner surface 46 and the tissue causes the tissue to fracture or otherwise break away from the body lumen for removal therefrom. With continued axial advancement of the catheter 2 and rotation of the tissue-removing element 4, the adjacent trailing secondary tissue-removing component 26 subsequently engages the tissue in much the same way as the cutting tooth 60 of the primary tissue-removing component 24. Thereafter, an adjacent primary tissue-removing component 24 engages the tissue, as disclosed above.

Figure 13:
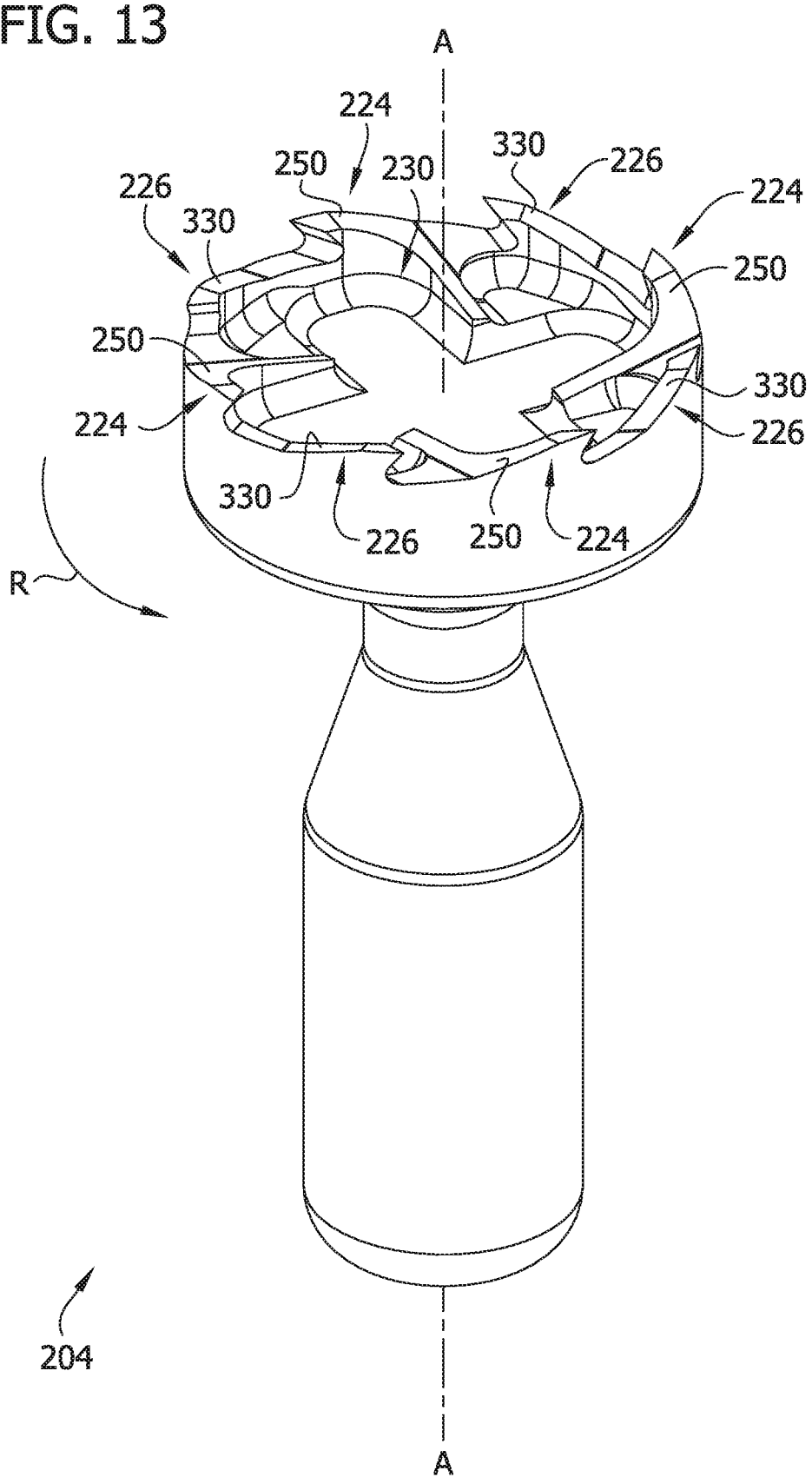
FIG. 13 is a perspective of another tissue-removing element.

Referring to FIG. 13, another embodiment of a tissue-removing element is generally indicated at reference numeral 204. The tissue-removing element includes four primary tissue-removing components 224 and four secondary tissue-removing components 226. The tissue-removing element 204 is substantially similar to the tissue-removing element 4, except for the differences that are, in part, apparent and, in part, pointed out hereinafter. Features of the tissue-removing element 204 are given the reference number of corresponding features of the tissue-removing element 4, plus 200. Like the tissue-removing element 4, the tissue-removing element 204 is configured for operative connection with the drive shaft 20 of the catheter 12 for rotation about an axis of rotation A in a cutting direction R. Unlike the primary and secondary tissue-removing components 24, 26 of the tissue-removing element 4, each tooth 224, 226 at its axial end 250, 330, respectively, is truncated to increase the sharpness of the leading edge 252 and lessen the relief angle of the leading portion. Referring to FIG. 14, the axial end surface 250 of the primary tissue-removing component 224 has a truncated leading portion 250A and a trailing portion 250B. The truncated leading portion 250A of the axial end surface 250 is positioned in one plane, and the trailing portion 250B is positioned in another, non-parallel plane. The axial end surface 330 of the secondary tissue-removing component 226 has a leading portion 330A and a trailing portion 330B. The leading portion 330A of the axial end surface 330 is positioned in one plane, and the trailing portion 330B is positioned in another, non-parallel plane.

Figure 15A:
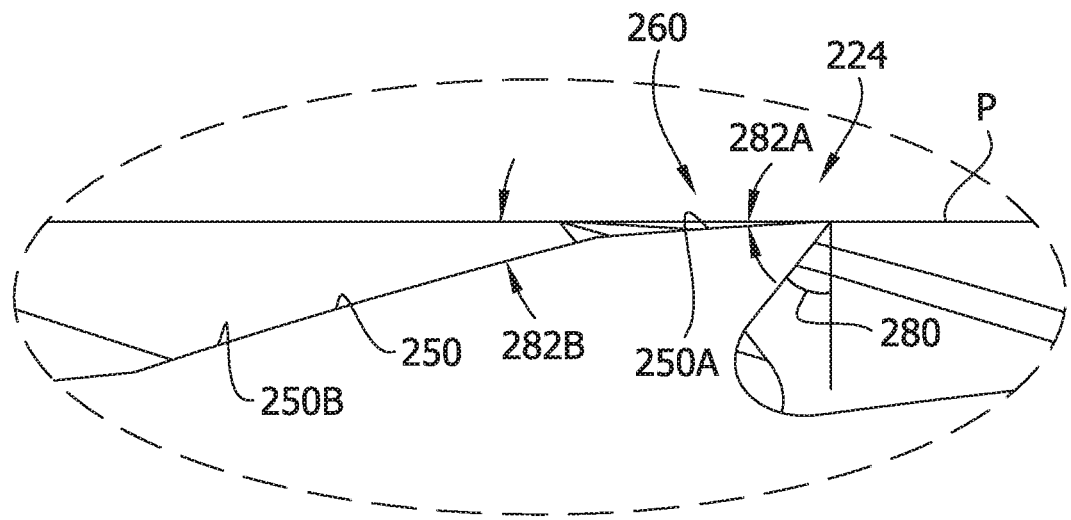
FIG. 15A is an enlarged fragmentary elevation of the tissue-removing element of FIG. 13 illustrating a primary tissue-removing component thereof.
Figure 15B:
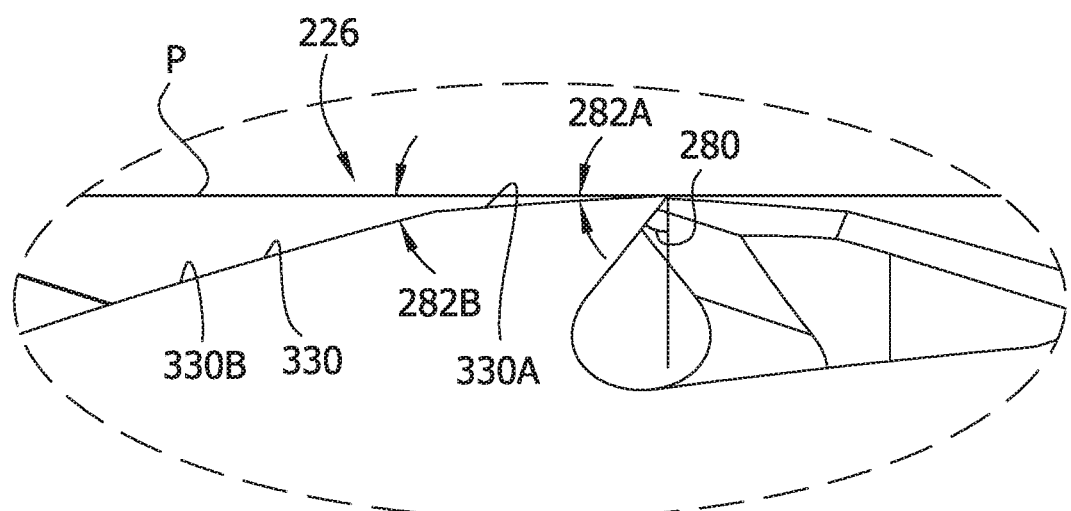
FIG. 15B is another enlarged fragmentary elevation of the tissue-removing element of FIG. 13 illustrating a secondary tissue-removing component thereof.

As shown in FIG. 15A, the leading portion 250A of the axial end surface 250 of the primary tissue-removing component 224 forms a first relief angle 282A with the cutting plane, and the trailing portion 250B forms a second relief angle 282B with the cutting plane P. Likewise, as shown in FIG. 15B, the leading portion 330A of the axial end surface 330 of the secondary tissue-removing component 226 forms a first relief angle 282A with the cutting plane, and the trailing portion 330B forms a second relief angle 282B with the cutting plane P. In the illustrated embodiment, the relief angles 282A, 282B are the same for the primary and secondary tissue-removing components 224, 226. The first relief angle 282A is less than the second relief angle 282B. In one or more embodiments, the first relief angle 282A may be from about 1° to about 5° and the second relief angle 282B may be from about 5° to about 60°. In the illustrated embodiment, the first relief angle 282A may be about 4° and the second relief angle 282B may be about 14°. The smaller relief angle 282A of the leading portions of the cutting teeth 260, 226 results in cutting teeth with more material at their leading portions. As a result, the leading portion of the cutting teeth 260, 226 are more robust than if the leading portions were relieved the same amount as the trailing portions. Thus, as in the illustrated embodiment, a high rake angle 280, as opposed to the first cutter embodiment 4, can be used without substantially affecting the robustness of the leading portions of the cutting teeth 260, 226. When a cutting tooth has a truncated leading portion with a relief angle from about 1° to about 5°, the rake angle for the tooth can be from about 5° to about 45°. In the illustrated embodiment, the rake angle 280 is about 25°.

In addition to enabling an increase in rake angle without adversely affecting the robustness of the leading portion of the corresponding cutting tooth 260, 226, the truncated leading portions 250A, 330A of the axial end surfaces 250, 330 of the cutting teeth 260, 226 may enhance engagement with hard tissue in a body lumen as compared with a non-truncated leading portion. For example when the leading portion of the cutting tooth 260, 226 is not truncated and the cutting tooth is formed with a large relief angle, the cutting tooth is prone to dig deeply into the hard tissue. However, when the cutting tooth 260, 226 engages hard tissue at too great a depth, it may be more difficult (e.g., require more force) to shear off the tissue as it rotates, and excessive torque caused by this force tends to cause the cutter to lose purchase with the tissue and thereby disengage. By comparison, the truncated leading portions of the cutting teeth 260, 226 reduce the depths at which the teeth engage hard tissue. This, in turn, reduces the force required to shear and bite through the hard tissue as the cutting teeth 260, 226 rotate, which increases the ability of the tissue-removing element 204 to remain engaged in the tissue.

A suitable method of making the tissue-removing element 204 is substantially similar to the method of making the tissue-removing element 4, discussed above. However, to form the axial end surface 250 of each primary tissue-removing component 224, a cutting implement can be oriented at a first selected angle relative the axis of rotation A and cutting plane P when used to form a leading portion 250A of an axial end surface 250 of a cutting tooth 260. The same cutting implement or another cutting implement can be oriented at a second selected angle relative the axis of rotation A and the cutting plane P to remove material from the blank to form a trailing portion 250B of the axial end surface 250 of the cutting tooth 260, as well as the axial end surface of the inner shearing member 262. The first selected angle is preferably chosen so a material-removal plane of the cutting implement is co-located with the leading portion 250A of the axial end surface 250. The second selected angle is preferably chosen so a material removal plane of the cutting implement is co-located with the trailing portion 250B of the axial end surface 250.

Figure 16:
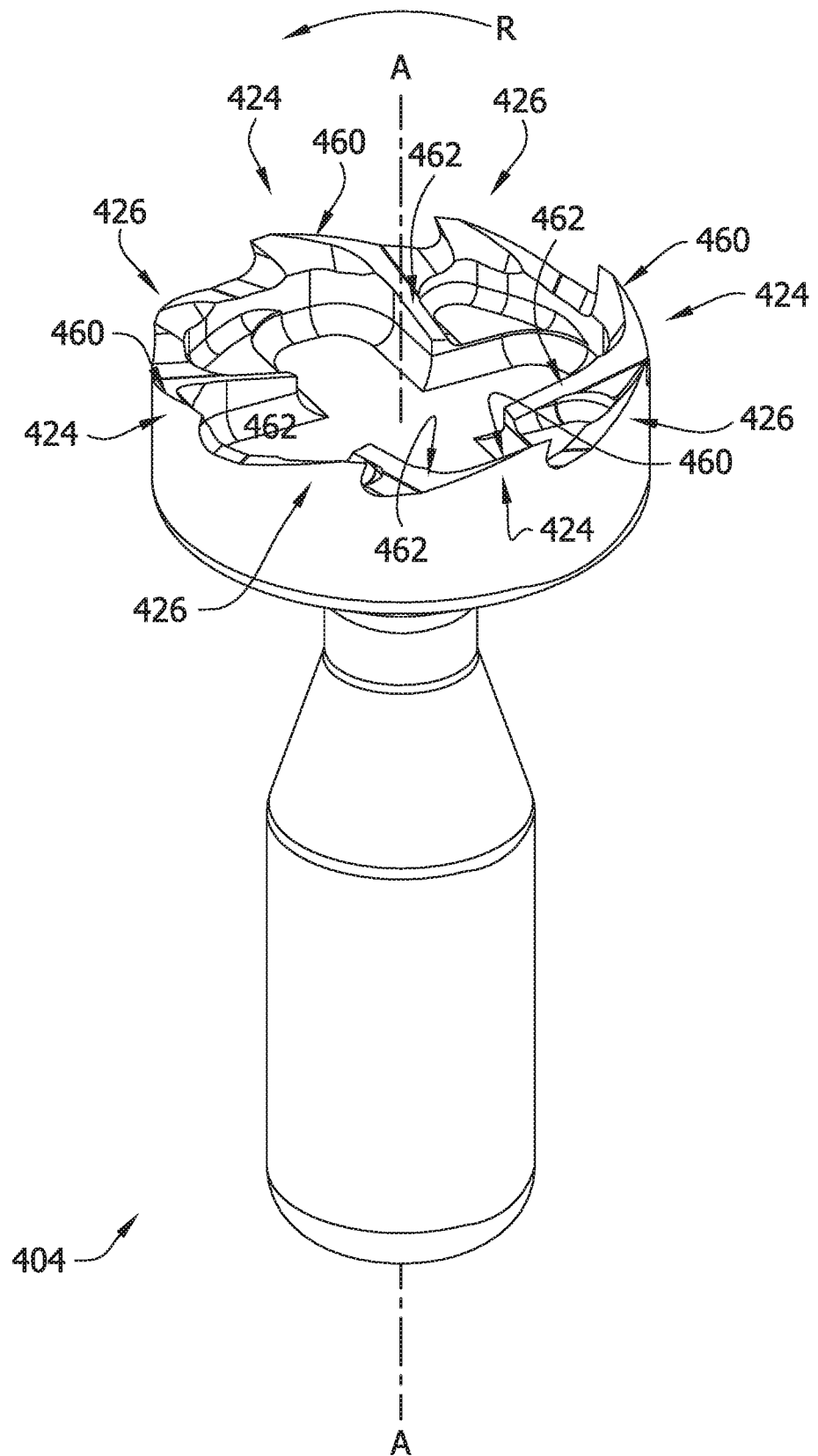
FIG. 16 is a perspective of another tissue-removing element.

Referring to FIG. 16, another embodiment of a tissue-removing element is generally indicated at reference numeral 404. The tissue-removing element 404 includes four primary tissue-removing components 424 and four secondary tissue-removing components 426. The tissue-removing element 404 is substantially similar to the tissue-removing element 4, except for the differences that are, in part, apparent and, in part, pointed out hereinafter. Features of the tissue-removing element 424 are given the reference number of corresponding features of the tissue-removing element 4, plus 400. Like the tissue-removing element 4, the tissue-removing element 404 is configured for operative connection with the drive shaft 20 of the catheter 12 for rotation about an axis of rotation A in a cutting direction R. In addition, like the tissue-removing element 4, each of the primary tissue-removing components 424 forms a cutting tooth 460 and an inner shearing member 462 and each of the secondary tissue-removing components 426 forms a cutting tooth that is substantially similar in form and function to the cutting tooth 460.

Figure 17:
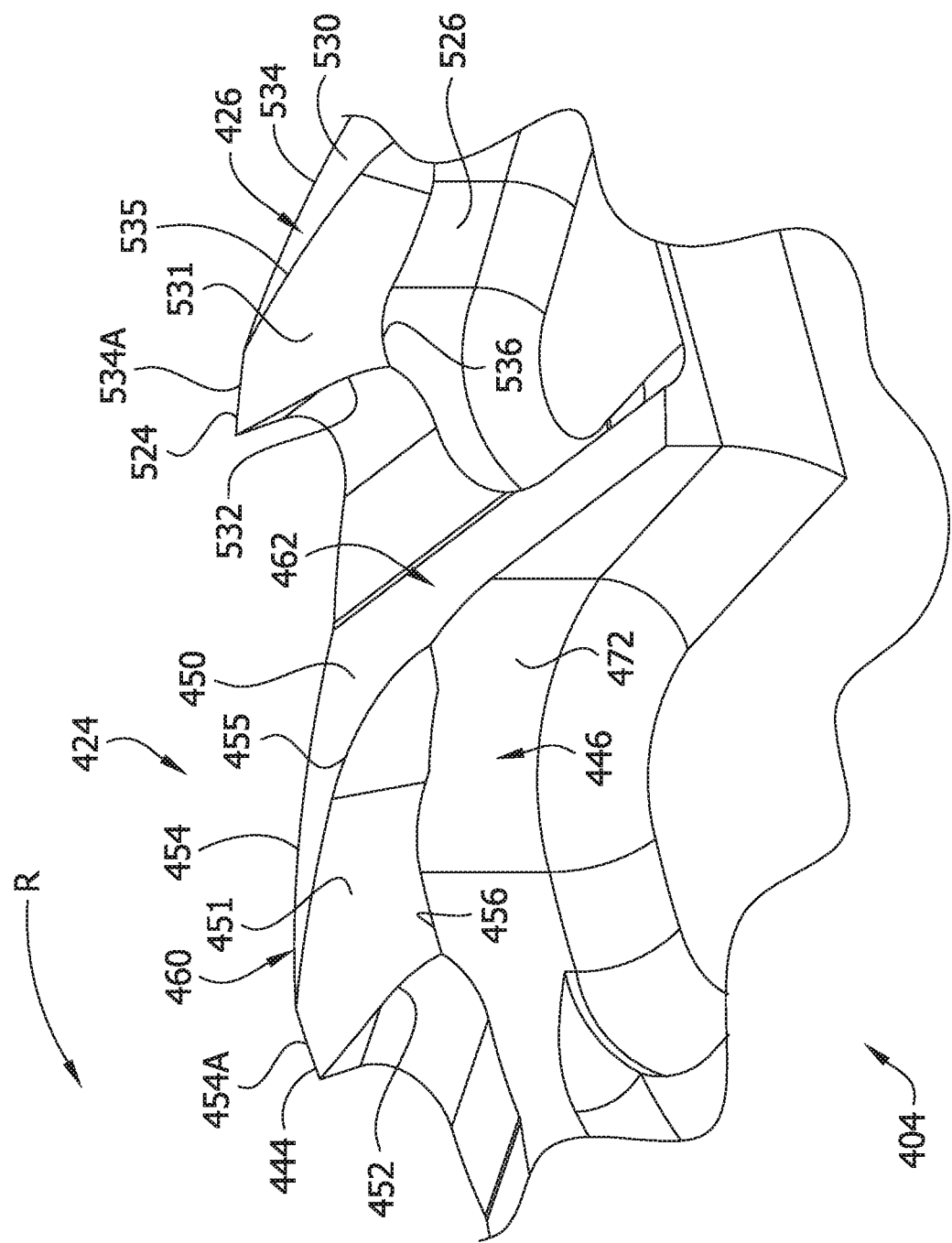
FIG. 17 is a fragmentary perspective of the tissue-removing element of FIG. 16.

As shown in FIG. 17, the axial end surface 450 at the leading portion of the primary tissue-removing component 424 has a beveled portion 451 extending from the radially outer edge 454 to the radially inner edge 456 and sweeping inward relative to the rotational axis A along an arcuate path from the leading edge 452 to the inner shearing member 462. In particular, the beveled portion 451 sweeps inward from the leading edge 452 to the arcuate portion 472 of the inner radial surface 446. The beveled portion 451 intersects the radially outer surface 444 along a sharp, outer fin edge 454A and intersects a trailing portion of the axial end surface 450 along an arcuate inner fin edge 455. The outer fin edge 454A is sharper than the radially outer edge 454 of the remainder (i.e., trailing portion) of the primary tissue-removing component 424. An arc length of the outer fin edge 454A may be from about 0.001 in to about 0.005 in (e.g., about 0.003 in) or from about 0.5% to about 3.5% of the outer radius of the tissue-removing element 404. The primary cutting tooth 460 has a wedge sectional shape and a more pointed distal tip and sharper radially outer edge (i.e., the outer fin edge 454A) as compared with the cutting tooth 60 of the tissue-removing element 4.

Other than the fact that the secondary tissue-removing component 426 does not include an impact component, the secondary tissue-removing component is substantially similar to the primary tissue-removing component 424. As shown in FIG. 17, the axial end surface 530 at the leading portion of the secondary tissue-removing component 426 has a beveled portion 531 extending from the radially outer edge 534 to the radially inner edge 536 and sweeping inward relative to the rotational axis A along an arcuate path from the leading edge 532 rearward. The beveled portion 531 intersects the radially outer surface 524 along a sharp, outer fin edge 534A and intersects a trailing portion of the axial end surface 530 along an arcuate inner edge 535. The outer fin edge 534A is sharper than the radially outer edge 534 of the remainder (i.e., trailing portion) of the secondary tissue-removing component 526. An arc length of the outer fin edge 534 may be from about 0.001 in to about 0.005 in (e.g., about 0.003 in) or from about 0.5% to about 3.5% of the outer radius of the tissue-removing element 404. The secondary cutting tooth 426 has a wedge sectional shape and a more pointed distal tip and sharper radially outer edge (i.e., the outer fin edge 534A) as compared with the cutting tooth 26 of the tissue-removing element 4.

It is believed that the beveled portions 451, 531 of the primary and secondary cutting teeth 460, 426 enhance engagement with tissue. The beveled portions 451, 531 slice into tissue as the tissue-removing element 404 rotates to part the tissue. In addition the cutting teeth 460, 426 are sufficiently robust at the tooth tip to engage the tissue without breaking. A larger arc length for the outer fine edge 454A, 534A is thought to improve the ability of the tissue-removing element 4 to remain engaged with tissue as it rotates and increase the slicing action of the cutting tooth 460, 426. However, the benefits of improved engagement should be balanced against the costs in efficiency, since a greater axial force may be necessary to cut through tissue at a given rate.

Figure 18:
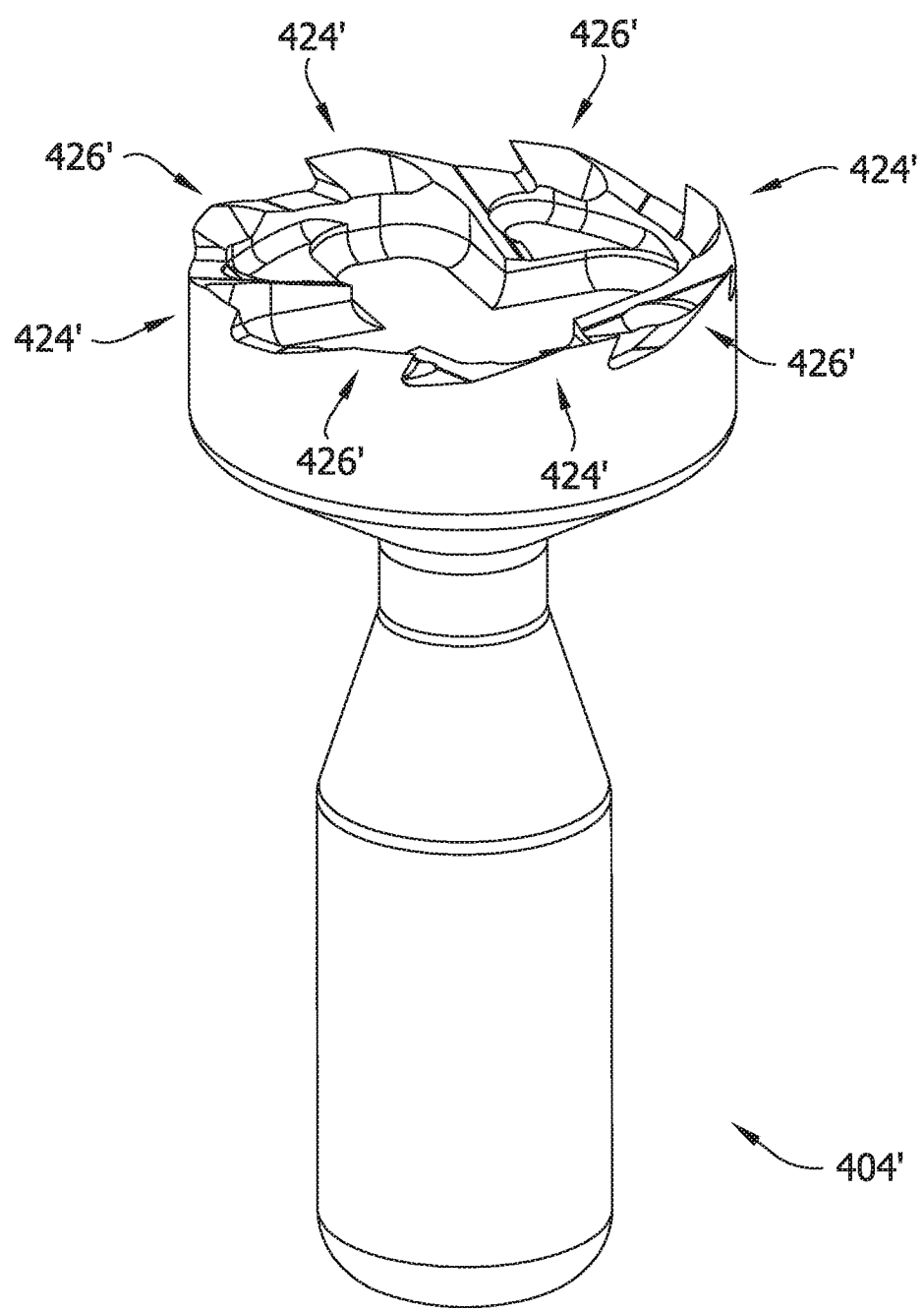
FIG. 18 is a perspective of another tissue-removing element.
Figure 19:
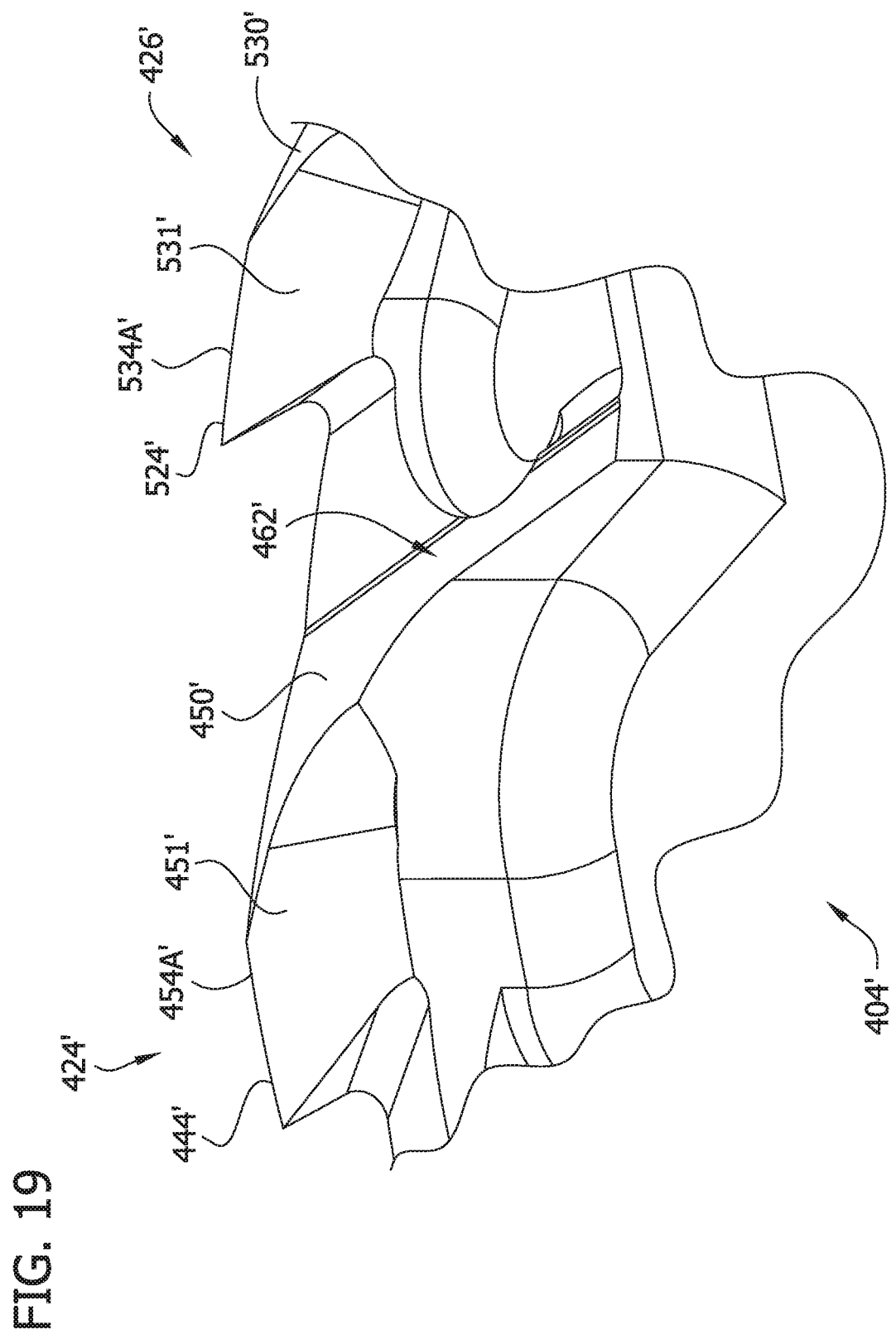
FIG. 19 is a fragmentary perspective of the tissue-removing element of FIG. 18.

Referring to FIGS. 18-19, another embodiment of a tissue-removing element is generally indicated at reference numeral 404'. This tissue-removing element 404' is substantially similar to the tissue-removing element 404, except for the differences that are, in part, apparent and, in part, pointed out hereinafter. Features of the tissue-removing element 404' are given the reference number of corresponding features of the tissue-removing element 404, followed by a prime symbol. Like the tissue-removing element 404, the primary tissue-removing component 424' of the tissue-removing element 404' includes a beveled portion 451' intersecting the radially outer surface 444' along a sharp, outer fin edge 454A'. Likewise, the secondary tissue-removing component 426' includes a beveled portion 531' intersecting the radially outer surface 524' along a sharp, outer fin edge 534A'. The difference between the embodiments is that the arc lengths of the outer fin edges 454A', 534A' of the present embodiment is greater than the arc lengths of the outer fin edges 454A, 534A of the tissue-removing element 404. For example, the arc lengths of the outer fin edges 454A', 534A' may be greater than about 0.003 in, such as from about 0.005 in to about 0.01 in, and in one embodiment, about 0.0075 in.

A suitable method of making the tissue-removing elements 404, 404' is substantially similar to the method of making the tissue-removing element 204. However, after forming the axial end surface 450, 450' of the primary tissue-removing component 424, 424' as described above with respect to the first embodiment, material is removed from the blank to sculpt the beveled portions 451, 451'. Likewise, after forming the axial end surface 530, 530' of a secondary tissue-removing component 426, 426', material is removed from the blank to sculpt the beveled portions 531, 531' of the secondary tissue-removing components.

Figure 20:
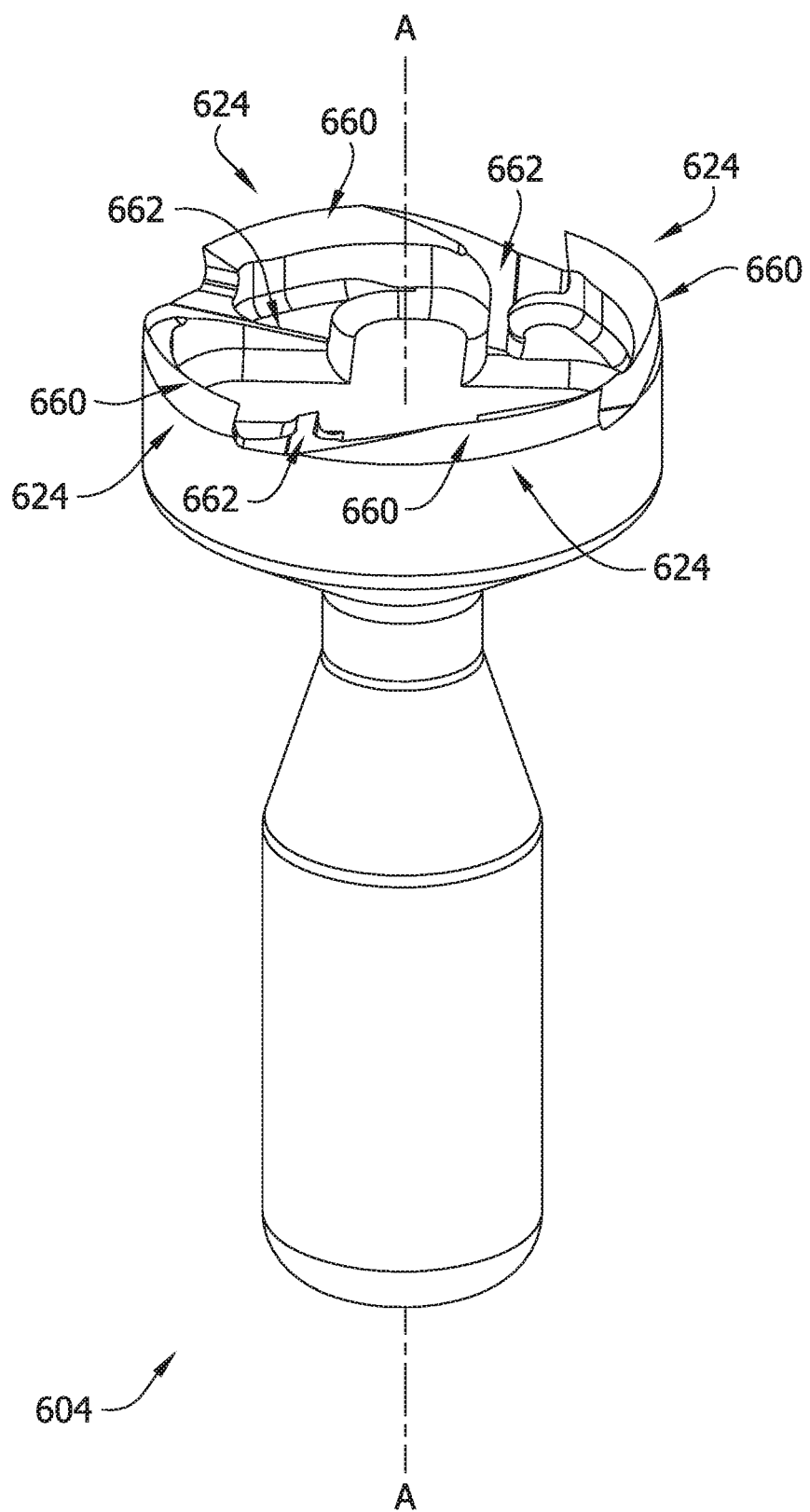
FIG. 20 is a perspective of another tissue-removing element.

Referring to FIG. 20, another tissue-removing element 604 includes four primary tissue-removing components 624 and no secondary tissue-removing components. The tissue-removing element 604 is similar in many respects to the tissue-removing element 404, except for the differences that are, in part, apparent and, in part, pointed out. Features of the tissue-removing element 604 are given the reference number of corresponding features of the tissue-removing element 404, plus 200. Like the tissue-removing element 404, the tissue-removing element 604 is configured for operative connection with the drive shaft 20 of the catheter 12 for rotation about an axis of rotation A in a cutting direction R. Like the primary tissue-removing component 424, the primary tissue-removing component 624 forms a cutting tooth 660 and an inner shearing member 662.

Figure 21:
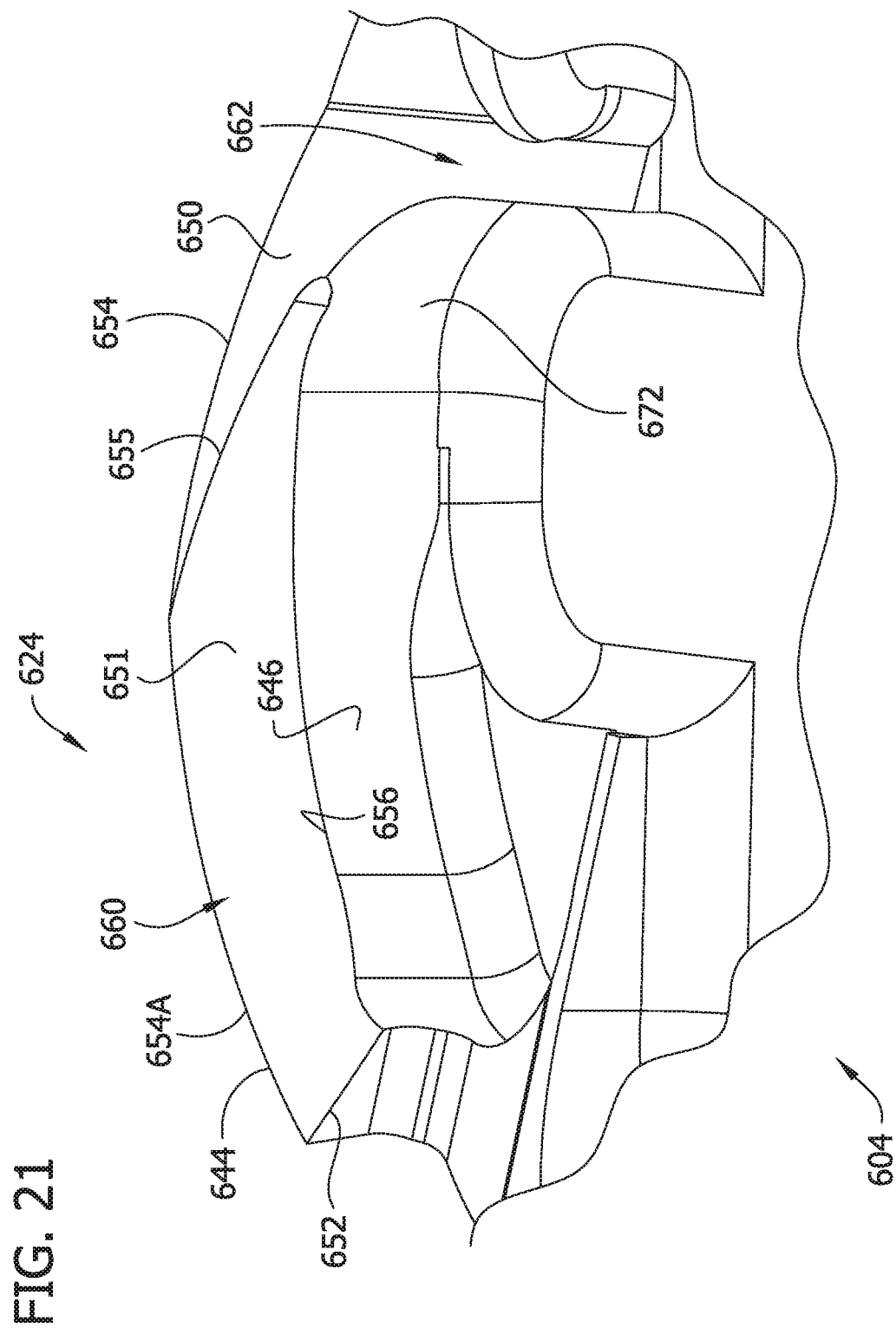
FIG. 21 is a fragmentary perspective of the tissue-removing element of FIG. 20.

As shown in FIG. 21, the axial end surface 650 at the leading portion of the primary tissue-removing component 624 has a beveled portion 651 extending from the radially outer edge 654 to the radially inner edge 656 and sweeping inward relative the rotational axis A along an arcuate path between the leading edge 652 and the inner shearing member 662. In particular, the beveled portion 651 sweeps inward between the leading edge 652 and the arcuate portion 672 of the inner radial surface 646. The beveled portion 651 intersects the radially outer surface 644 along a sharp, outer fin edge 654A and intersects a trailing portion of the axial end surface 650 along an arcuate inner fin edge 655. The outer fin edge 654A is sharper than the trailing portion of the radially outer edge 654.

Figure 22:
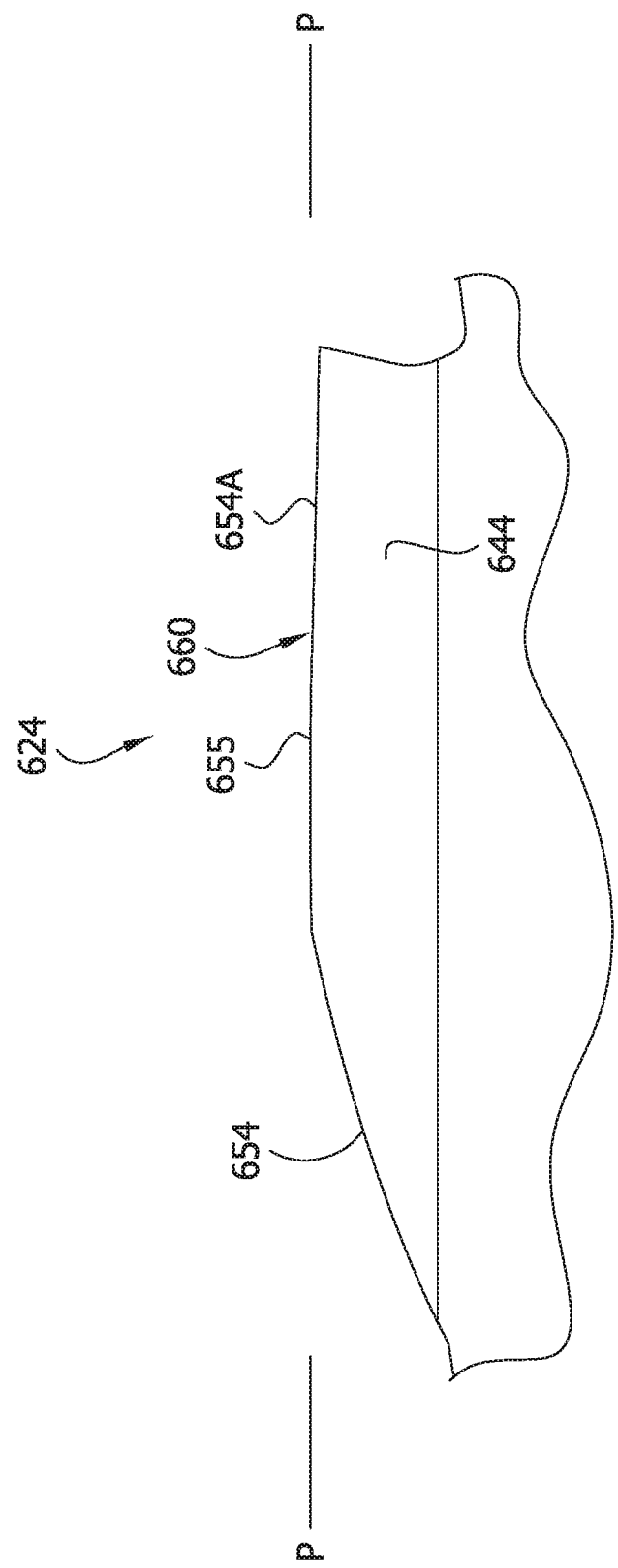
FIG. 22 is a fragmentary elevation of the tissue-removing element of FIG. 20.

In one or more embodiments, the arc length of the outer fin edge 654A is from about 0.0255 inches to about 0.05 inches or from about 12.5% to about 24% of the outer radius of the tissue-removing element 504. In the illustrated embodiment the outer fin edge 654A is about 0.0235 inches. The relatively long arc length of the outer fin edge 654A allows the cutting tooth 660 to continuously engage and slice through tissue for nearly a quarter of a rotation of the tissue-removing element 604 around its cutting axis A. As shown best in FIG. 22, the outer fin edge 654A has a zero-degree relief angle relative the cutting plane P. However, as discussed below, the outer fin edge can have a non-zero relief angle without departing from the scope of the invention.

Figure 23:
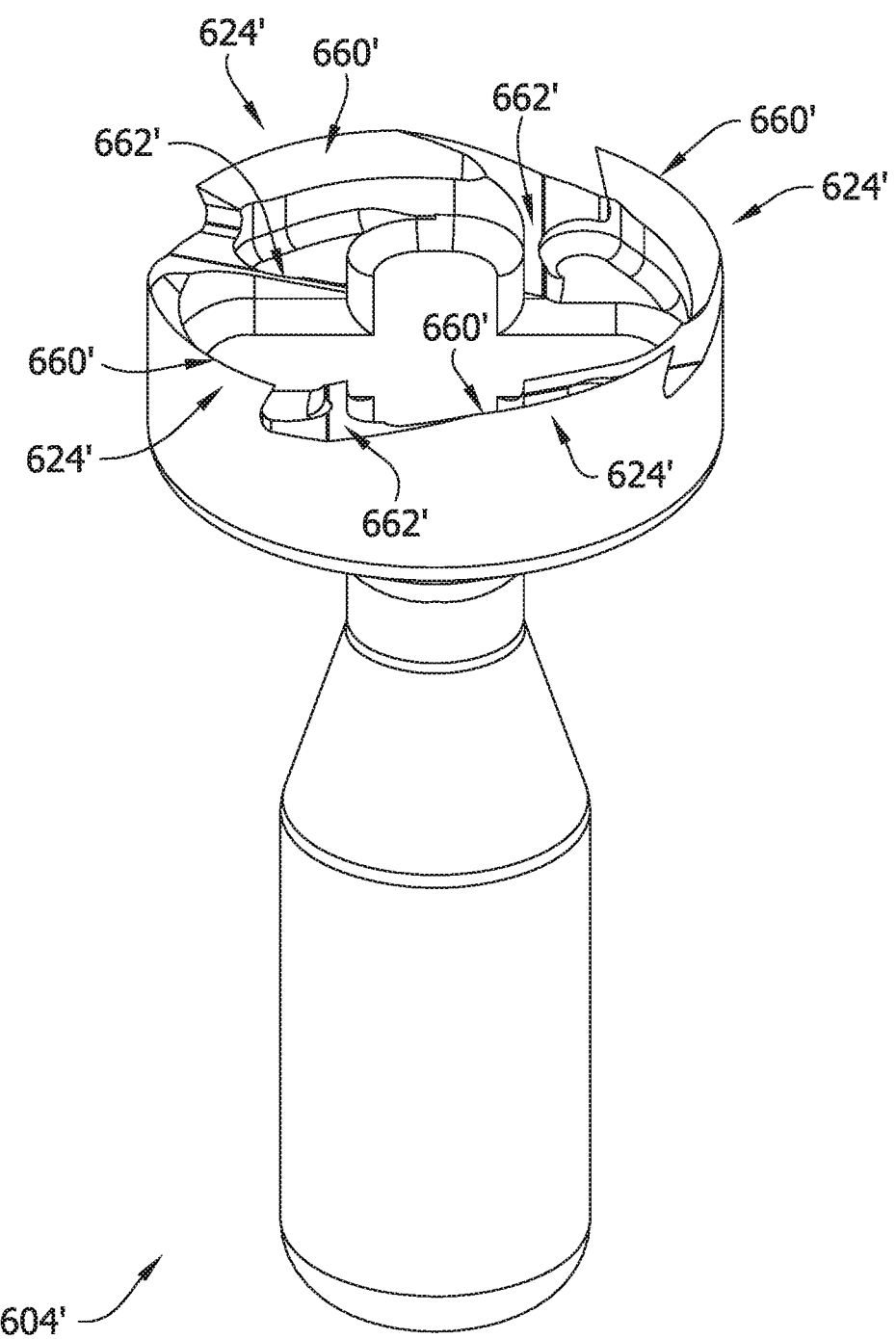
FIG. 23 is a perspective of another tissue-removing element.
Figure 24:
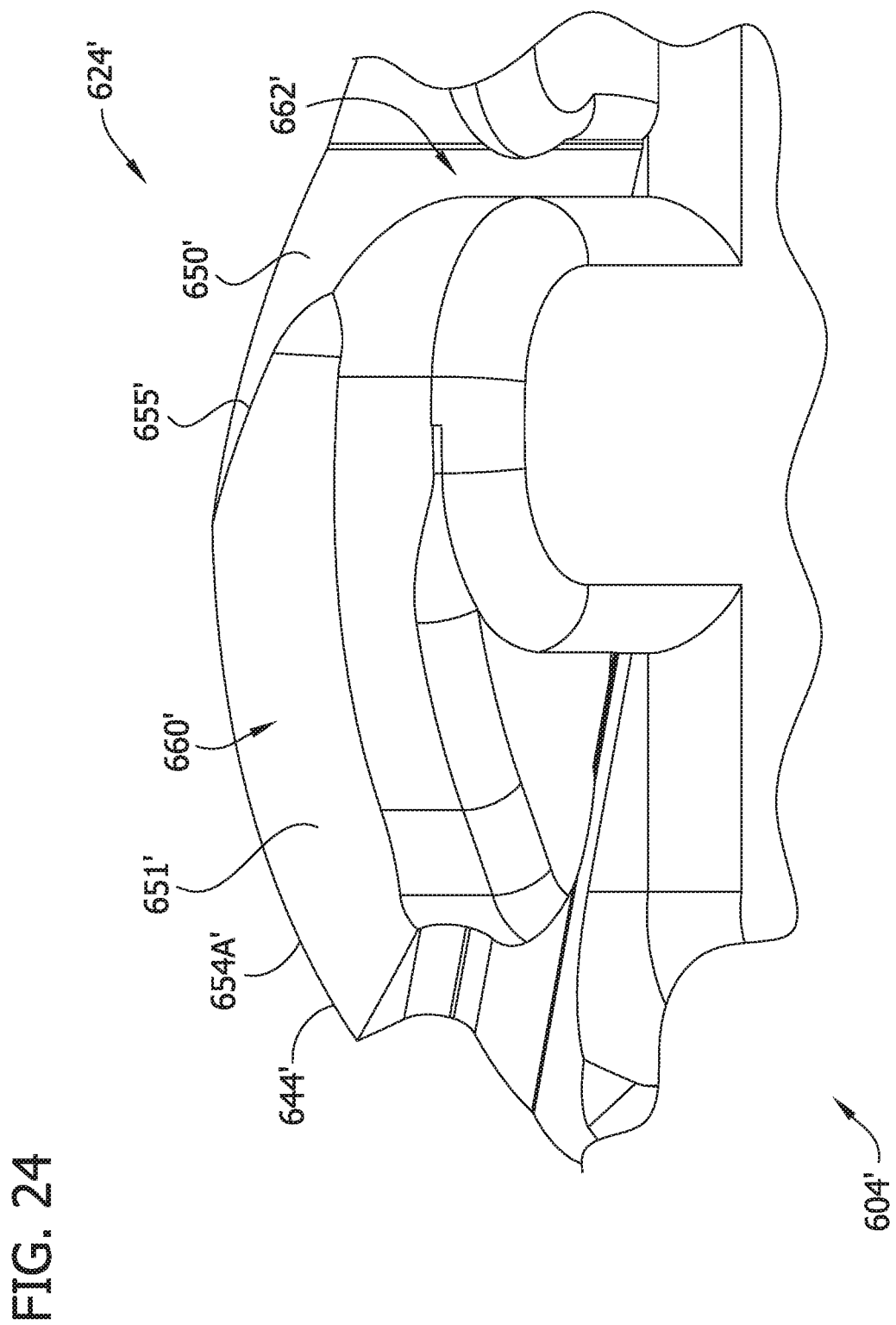
FIG. 24 is a fragmentary perspective of the tissue-removing element of FIG. 23.
Figure 25:
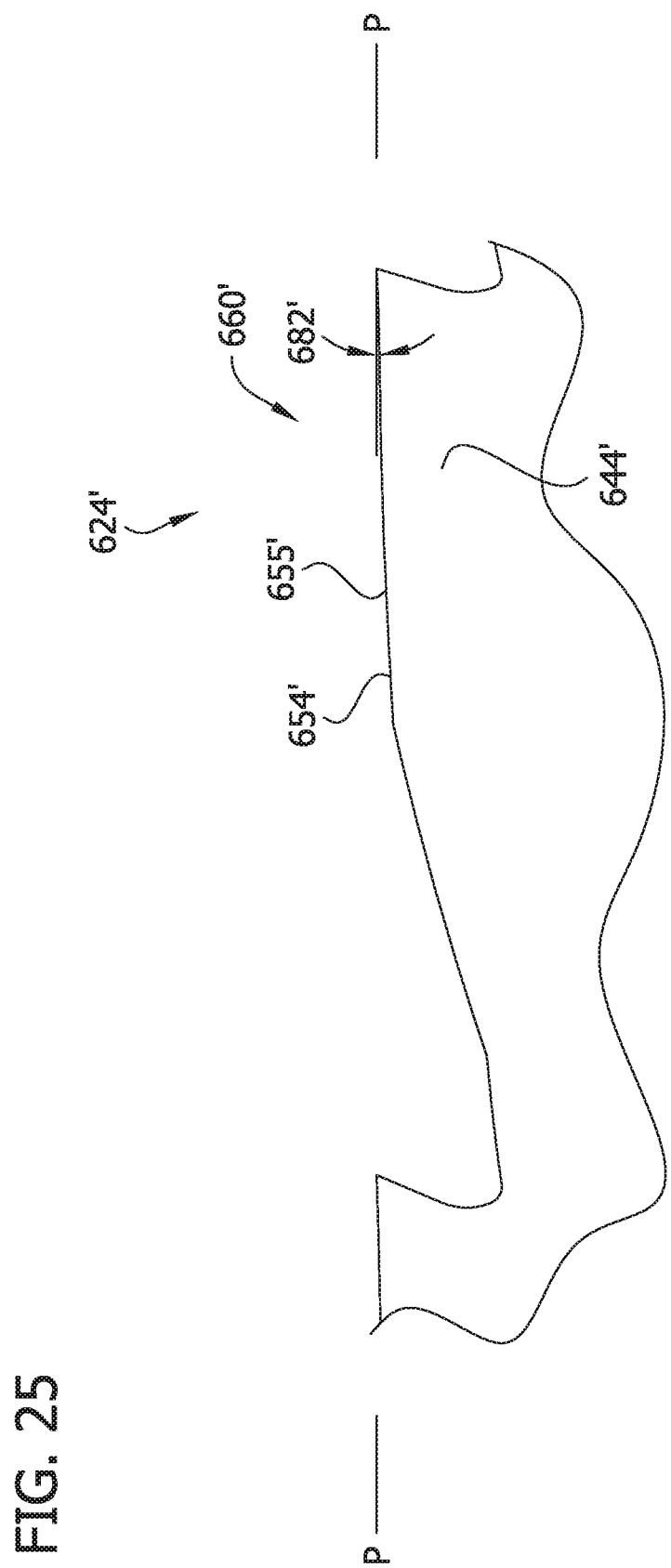
FIG. 25 is a fragmentary elevation of the tissue-removing element of FIG. 23.

Referring to FIGS. 23-25, a tissue-removing element 604' is substantially similar to the tissue-removing element 604, except for the differences that are, in part, apparent and, in part, pointed out hereinafter. Features of the tissue-removing element 604' are given the reference number of corresponding features of the tissue-removing element 604, followed by a prime symbol. Like the tissue-removing element 604, the tissue-removing element 604' includes four primary tissue-removing components 624' and zero secondary tissue-removing components. Each primary tissue-removing component 624' forms a cutting tooth 660' and an inner shearing member 662'. The primary tissue-removing component 624' includes a beveled portion 651' that intersects the radially outer surface 644' along a sharp outer fin edge 654A' and intersects the axial end surface 650' along an inner fin edge 655'. However, as shown in FIG. 25, unlike the outer fin edge 654A, the outer fin edge 654A' has a relief angle 682' of about 1° relative the cutting plane P, rather than about 0°. In one or more embodiments, the outer fin edge 645A' can have a relief angle 682' between about 1° and about 10°.

Where dimensional ranges are cited in the present disclosure, it should be understood that the range is inclusive of the end points of the range, unless otherwise indicated. For example, a range of "between about 1 inch and about 2 inches" includes lengths of about 1 inch and about 2 inches and all of the lengths between those two end points of the range.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue from a biological lumen, the tissue-removing catheter comprising:
a rotatable shaft; and
a tissue-removing element coupled to the rotatable shaft for rotating the tissue-removing element about an axis of rotation, the tissue-removing element having opposite first and second axial ends and an exterior surface extending generally axially from the first axial end to the second axial end and extending circumferentially about the axis of rotation, the tissue-removing element comprising:
a plurality of primary tissue-removing components at the first axial end of the tissue-removing element and spaced apart from one another around the axis of rotation, each primary tissue-removing component having a leading surface extending generally axially, a radially outer surface extending generally axially, a radially inner surface extending generally axially and generally inward relative to the axis of rotation from adjacent a leading end toward a trailing end thereof, and an axial end surface intersecting the leading, the radially outer, and the radially inner surfaces at respective leading, radially outer, and radially inner edges,
wherein the leading surface, the leading edge and leading portions of the radially outer surface, the radially inner surface, and the axial end surface at least partially forms a cutting tooth adapted to cut tissue as the tissue-removing element rotates to facilitate removal of tissue,
wherein trailing portions of the radially outer surface, the radially inner surface, and the axial end surface at least partially forms an inner shearing member adapted to impact tissue and shear the impacted tissue radially inwardly as the tissue-removing element rotates to facilitate removal of hard tissue, wherein the radially outer surface of each primary tissue-removing component forms a respective portion of the exterior surface of the tissue-removing element, and wherein the radially outer surface of each primary tissue-removing component intersects the leading surface of the respective primary tissue-removing component at an outer axial edge extending generally axially, wherein the leading surface of each primary tissue-removing component intersects the respective radially inner surface at an intermediate axial edge extending generally axially, wherein the intermediate axial edge intersects the respective radially inner edge at a radially inner axial end corner of the cutting tooth, and wherein the radially inner edge extends contiguously from the radially inner axial end corner of the cutting tooth to the trailing end of the radially inner surface and forms a leading axial edge of the inner shearing member located radially inward of the radially inner axial end corner of the cutting tooth.

2. The tissue-removing catheter set forth in claim 1, wherein the cutting tooth and the inner shearing member of each primary tissue-removing component are integrally formed as a single piece of material.

3. The tissue-removing catheter set forth in claim 2, wherein the primary tissue-removing components are integrally formed as a single piece of material.

4. The tissue-removing catheter set forth in claim 1, wherein the radially inner surface of each primary tissue-removing component has an arcuate portion curving inward relative to the axis of rotation from adjacent the leading end toward the trailing end thereof.

5. The tissue-removing catheter as set forth in claim 4, wherein the tissue-removing element has an outer surface defining a radius of the tissue-removing element, wherein the arcuate portion of the radially inner surface of at least one of the primary tissue-removing components has a radius of curvature that is from about 1% to about 50% of the radius of the tissue-removing element.

6. The tissue-removing catheter set forth in claim 4, wherein the arcuate portion of the radially inner surface of each primary tissue-removing component forms part of the inner shearing member.

7. The tissue-removing catheter set forth in claim 6, wherein the radially inner surface of each primary tissue-removing component has a transverse portion extending generally inward relative to the axis of rotation from a trailing end of the arcuate portion toward the trailing end of the radially inner surface, the transverse portion extending generally transverse to the cutting tooth.

8. The tissue-removing catheter as set forth in claim 7, wherein the tissue-removing element has an outer surface defining a radius of the tissue-removing element, wherein the transverse portion of the radially inner surface of at least one of the primary tissue-removing components has a length that is from about 1% to about 75% of the radius of the tissue-removing element.

9. The tissue-removing catheter set forth in claim 7, wherein the transverse portion of the radially inner surface of at least one of the primary tissue-removing components extends generally in an impact plane that is offset from the axis of rotation in a direction perpendicular to the impact plane.

10. The tissue-removing catheter as set forth in claim 9, wherein the impact plane is offset from the axis of rotation in by an offset distance of about 0.010 inches (0.254 mm).

11. The tissue-removing catheter set forth in claim 1, further comprising a plurality of secondary cutting components at the first axial end of the body and spaced apart from one another around the axis of rotation, each secondary cutting component being disposed between adjacent primary tissue-removing components and having a leading surface extending generally axially, a radially outer surface extending generally axially, a radially inner surface extending generally axially and generally inward relative to the axis of rotation from adjacent a leading end toward a trailing end thereof, and an axial end surface intersecting the leading, the radially outer, and the radially inner surfaces at respective leading, radially outer, and radially inner edges, wherein the leading surface, the leading edge, and leading portions of the radially outer surface, the radially inner surface, and the axial end surface at least partially forms a cutting tooth adapted to cut tissue as the tissue-removing element rotates to facilitate removal of tissue.

12. The tissue-removing catheter set forth in claim 1, wherein the leading surface of each primary tissue-removing component defines a positive rake angle of the corresponding cutting tooth.

13. The tissue-removing catheter as set forth in claim 12, wherein the rake angle of at least one of the cutting teeth is in a range of from about +5° to about +35°.

14. The tissue-removing catheter set forth in claim 1, wherein the leading edge of each primary tissue-removing component defines a fleam angle of the cutting tooth, the fleam angle being greater than 0 degrees.

15. The tissue-removing catheter as set forth in claim 14, wherein the fleam angle of at least one of the cutting teeth is in a range of from about from about 1° to about 60°.

16. The tissue-removing catheter set forth in claim 1, wherein the axial end surface of each primary tissue-removing component has a tilt angle relative to a plane that is orthogonal to the axis of rotation, wherein the tilt angle is constant from the corresponding cutting tooth to the corresponding inner shearing member of the primary tissue-removing component.

17. The tissue-removing catheter set forth in claim 1, wherein the tissue-removing element has an outer surface defining a radius of the tissue-removing element, and the inner shearing member of at least one of the primary tissue-removing components has a radially innermost point with respect to the axis of rotation, wherein said shearing member has a radial length that extends from the radially innermost point to the outer surface of the tissue-removing element along an imaginary line that passes through both the axis of rotation and the innermost point in a plane perpendicular to the axis of rotation, wherein the radial length is less than the radius of the tissue-removing element.

18. The tissue-removing catheter as set forth in claim 17, wherein the radial length is from about 10% to about 80% of the radius of the tissue-removing element.

* * * * *